(12) United States Patent
Diep et al.

(10) Patent No.: US 9,221,821 B2
(45) Date of Patent: Dec. 29, 2015

(54) METHODS FOR THE SYNTHESIS OF 1,3-SUBSTITUTED AMINOURACILS AND OTHER XANTHINE-RELATED COMPOUNDS

(71) Applicant: Forest Laboratories Holdings Limited, Hamilton (BM)

(72) Inventors: Nhut Diep, Hauppauge, NY (US); Yuriy B. Kalyan, Staten Island, NY (US)

(73) Assignee: Forest Laboratories Holdings, Limited (BM)

( * ) Notice: Subject to any disclaimer, the term of this patent is extended or adjusted under 35 U.S.C. 154(b) by 37 days.

(21) Appl. No.: 13/907,239

(22) Filed: May 31, 2013

(65) Prior Publication Data

US 2013/0324724 A1    Dec. 5, 2013

Related U.S. Application Data

(60) Provisional application No. 61/655,707, filed on Jun. 5, 2012.

(51) Int. Cl.
| | |
|---|---|
| C07D 473/06 | (2006.01) |
| C07D 239/22 | (2006.01) |
| C07D 401/12 | (2006.01) |
| C07D 239/545 | (2006.01) |

(52) U.S. Cl.
CPC ............ C07D 473/06 (2013.01); C07D 239/22 (2013.01); C07D 239/545 (2013.01); C07D 401/12 (2013.01)

(58) Field of Classification Search
CPC ... C07D 473/06; C07D 239/22; C07D 401/12
USPC ........................................ 544/269
See application file for complete search history.

(56) References Cited

U.S. PATENT DOCUMENTS

| | | |
|---|---|---|
| 4,469,698 A | 9/1984 | Philippossian et al. |
| 7,601,723 B2 | 10/2009 | Wang et al. |
| 7,943,625 B2 | 5/2011 | Tidén |
| 8,044,061 B2 | 10/2011 | Müller et al. |
| 8,071,586 B2 | 12/2011 | Aebi et al. |
| 8,101,655 B2 | 1/2012 | Smith et al. |
| 8,163,761 B2 | 4/2012 | Ng et al. |

OTHER PUBLICATIONS

Elzein, E., "Discovery of a novel A2B adenosine receptor antagonist as a clinical candidate for chronic inflammatory airway diseases." Journal of medicinal chemistry 51.7 (2008): 2267-2278.*
Greene, T.W., (Greene's Protective Groups in Organic Synthesis, Fourth Edition, John Wiley and Sons, published online Apr. 10, 2006; Chapter 7, p. 828-833.*
Reich, H.J.,Handbook of reagents for organic synthesis—Acidic and basic reagents, 1999, John Wiley and Sons. p. 309-311, 343-346.*
Bénard, S., "Copper-mediated N-cyclopropylation of azoles, amides, and sulfonamides by cyclopropylboronic acid." (2008): 6441-6444.*
Tsuritani, T., "N-Cyclopropylation of indoles and cyclic amides with copper (II) reagent." Organic letters 10.8 (2008): 1653-1655.*
Katritzky, AR, et al., Comprehensive Organic Functional Group Transformations, vol. 1, Elsevier, 1995, p. 149; [Retrieved Oct. 16, 2013]. Retrieved from the Internet: ,URL: http://books.google.com/ >.
International Search Report and Written Opinion corresponding to International Application No. PCT/US13/43880, mailed Oct. 29, 2013; 11 pages.
PCT Recordation of Search History, 16 Pages.
US 8,148,383, 04/2012, Maekawa et al. (withdrawn)

* cited by examiner

Primary Examiner — Samantha Shterengarts
Assistant Examiner — Matt Mauro
(74) Attorney, Agent, or Firm — Carter, DeLuca, Farrell & Schmidt, LLP

(57) ABSTRACT

Methods for the synthesis of disubstituted aminouracils and xanthine and/or xanthine-related compounds are provided.

35 Claims, No Drawings

METHODS FOR THE SYNTHESIS OF 1,3-SUBSTITUTED AMINOURACILS AND OTHER XANTHINE-RELATED COMPOUNDS

CROSS REFERENCE TO RELATED APPLICATIONS

This application claims priority to, and the benefit of, U.S. Provisional Patent Application Ser. No. 61/655,707, filed Jun. 5, 2012, the entire contents of which are incorporated by reference herein.

FIELD OF THE INVENTION

The present disclosure describes methods for the synthesis of substituted aminouracils and xanthine and/or xanthine-related compounds. More specifically, the methods described herein produce selective 1,3 disubstituted 6-aminouracils which can be further processed to form a wide variety of xanthine and/or xanthine-related compounds.

BACKGROUND OF THE INVENTION

Disubstituted aminouracils may be used to form xanthine and xanthine-related compounds. As illustrated below, one method for the synthesis of disubstituted aminouracils may include the process of condensation of a disubstituted urea (A) with cyanoacetic acid in acetic anhydride (1) followed by base-promoted cyclization (2).

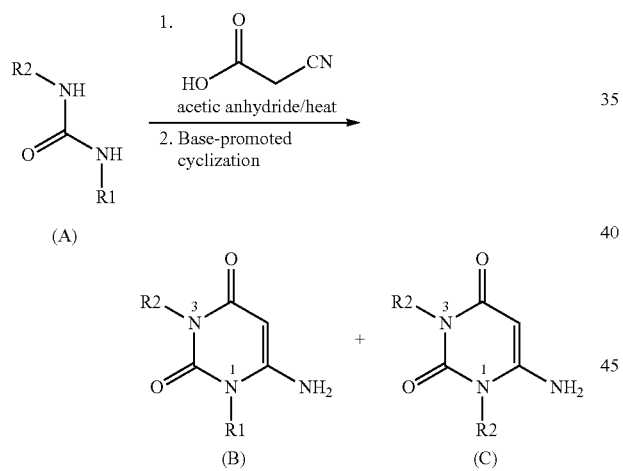

Such a method produces a mixture of two isomeric disubstituted aminouracils (B) and (C). Thus purification may often be necessary to obtain a single isomer of the disubstituted aminouracil prior to additional processing to form a xanthine and/or xanthine-related compound. In fact, in some instances, obtaining a single isomer of the disubstituted aminouracil may not be feasible via condensation, since the condensation process may not be sufficiently selective and the ratio amounts of the two isomeric disubstituted aminouracils (B) and (C) may depend upon the relative size of the substituents and/or functional groups of the disubstituted urea (A).

It would be beneficial to provide a selective method for the synthesis of a variety of substituted aminouracils, and specifically disubstituted aminouracils, in order to selectively place functional groups at specific positions of the aminouracils prior to the formation of substituted xanthine and/or xanthine-related compounds.

SUMMARY

The present disclosure describes methods for the selective synthesis of a wide-range of substituted aminouracil compounds and specifically 1,3-disubstituted 6-aminouracils, which may be further processed to form a wide-range of xanthine and/or xanthine-related compounds.

In embodiments, a process is described for preparing a compound of formula I:

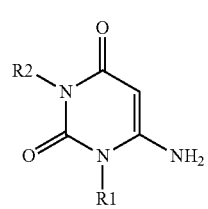

wherein:
$R^1$ and $R^2$ are as described hereinbelow,
the process including:
a) reacting a monosubstituted urea of formula II

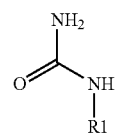

with ethyl-2-cyanoacetate in the presence of an alkoxide to produce an aminouracil of formula IIIa,

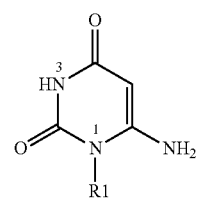

b) reacting the aminouracil of formula IIIa with dimethyl formamide-dimethyl acetal to produce a compound of formula IV,

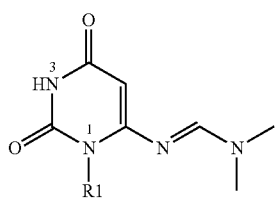

c) reacting the compound of formula IV with either: a $R^2$-boronic acid, a first metal carbonate and a copper catalyst; a $R^2$-halide, a second metal carbonate and an aprotic solvent; or, $R^2$—CO—W, a third metal carbonate and an aprotic solvent, to produce a compound of formula V, and,

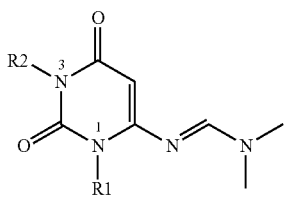

wherein W is a leaving group, d) reacting the compound of formula V with an inert solvent and a metal hydroxide to produce the compound of formula I.

In embodiments, a process is described for preparing a xanthine compound of formula IX:

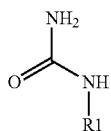

wherein:
$R^1$, $R^2$ and R' are as described hereinbelow
the process including:
a) reacting a monosubstituted urea of formula II

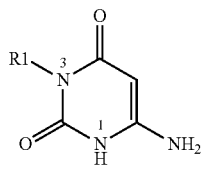

with 3-amino-3-ethoxy-acrylate in the presence of an alkoxide to produce an aminouracil of formula IIIb,

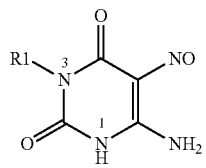

b) reacting the aminouracil of formula IIIb with a nitration agent in the presence of an acid to produce a compound of formula X,

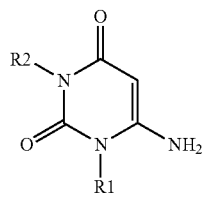

c) reacting the compound of formula X with a reducing agent to produce a compound of formula XI, and,

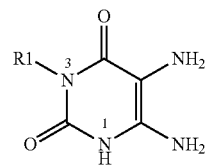

d) reacting the compound of formula XI with an acylating agent of the formula R'—CO—W' to produce a compound of formula XII

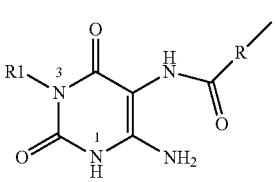

wherein W' is a leaving group, e) reacting the compound of formula XII with a $R^2$-halide, metal carbonate, and an aprotic solvent to produce a compound of formula XIII, and,

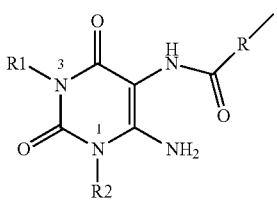

f) reacting the compound of formula XIII with an inert solvent and a metal hydroxide to produce the xanthine compound of formula IX.

DETAILED DESCRIPTION

The present disclosure provides methods for the synthesis of a wide-range of selectively substituted aminouracil compounds and specifically 1,3-disubstituted 6-aminouracils, which may be further processed to form a wide-range of xanthine and/or xanthine-related compounds. The present methods avoid formation of isomeric mixtures thus providing for more efficient methods of purification and production.

In embodiments, there is provided a first process for preparing a compound of formula I:

wherein:
$R^1$ and $R^2$ are independently hydrogen, $(C_1$-$C_8)$alkyl, $(C_3$-$C_8)$alkenyl, $(C_3$-$C_8)$alkynyl, $(C_1$-$C_8)$alkoxy, $(C_3$-$C_8)$cycloalkyl, $(C_3$-$C_8)$cycloalkyl$(C_1$-$C_8)$alkyl-, $(C_4$-$C_{10})$heterocycle, $(C_4$-$C_{10})$heterocycle$(C_1$-$C_8)$alkyl-, $(C_6$-$C_{10})$ aryl, $(C_6-C_{10})$aryl$(C_1-C_8)$alkyl-, $(C_5-C_{10})$hetero aryl, or $(C_5-C_{10})$heteroaryl$(C_1-C_8)$alkyl-;
the process including:
a) reacting a monosubstituted urea of formula II

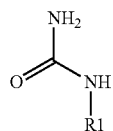
II with ethyl-2-cyanoacetate in the presence of an alkoxide to produce an aminouracil of formula IIIa,

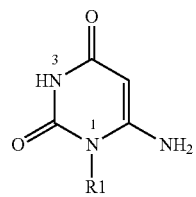
IIIa b) reacting the aminouracil of formula III with dimethyl formamide-dimethyl acetal to produce a compound of formula IV,

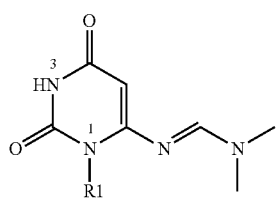
IV c) reacting the compound of formula IV with either: a $R^2$-boronic acid, a first metal carbonate and a copper catalyst; a $R^2$-halide, a second metal carbonate and an aprotic solvent; or, $R^2$—CO—W, a third metal carbonate and an aprotic solvent, to produce a compound of formula V, and,

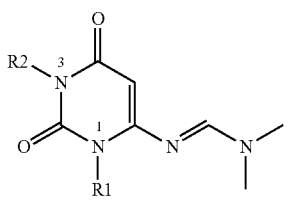
V wherein W is a leaving group,
d) reacting the compound of formula V with an inert solvent and a metal hydroxide to produce the compound of formula I.

In embodiments, the alkoxide of the first process includes at least one metal alkoxide, e.g., sodium ethoxide, potassium ethoxide, calcium ethoxide, potassium tert-butoxide and sodium tert-butoxide, and combinations thereof. In embodiments, the metal alkoxide is sodium ethoxide.

In embodiments, step b) of the first process may be exothermic and performed at a temperature ranging from about 0° C. to about 100° C., e.g., about 40° C.

In embodiments, the compound of formula IV may be combined with a $R^2$-boronic acid, a first metal carbonate and a copper catalyst to produce the compound of formula V.

In embodiments, the compound of formula IV may be combined with $R^2$-halide, a second metal carbonate and an aprotic solvent to produce the compound of formula V.

In embodiments, the compound of formula IV may be combined with $R^2$—CO—W, a third metal carbonate and an aprotic solvent to produce the compound of formula V.

Some non-limiting examples of suitable copper catalysts include copper bromide, copper iodide, copper acetate, copper chloride, copper carbonate, copper nitrate, copper sulfate, copper hydroxide, copper methylate, and combinations thereof. In embodiments, the copper catalyst is copper acetate.

Some non-limiting examples of first, second and third metal carbonates include sodium carbonate, potassium carbonate, lithium carbonate, cesium carbonate, sodium bicarbonate, potassium bicarbonate, lithium bicarbonate, cesium bicarbonate, and combinations thereof. In embodiments, the first metal carbonate is sodium carbonate. In embodiments, the second metal carbonate is potassium carbonate.

Some non-limiting examples of aprotic solvents include dimethyl sulfoxide, acetonitrile, acetone, dimethylformamide, ethyl acetate, tetrahydrofuran, dichloromethane, and combinations thereof. In embodiments, the aprotic solvent of step c) of the first process is dimethylformamide.

In embodiments, the compound of formula IV may be combined with a $R^2$-boronic acid, copper acetate (catalytic) and sodium carbonate in the presence of an amine ligand to produce the compound of formula V. In embodiments, the compound of formula IV may be combined with a $R^2$-halide, dimethylformamide and potassium carbonate to produce the compound of formula V. In embodiments, the compound of formula IV may be combined with a $R^2$—CO—Cl and potassium carbonate to produce the compound of formula V.

In embodiments, the compound of formula V may combined with at least one metal hydroxide, e.g., sodium hydroxide, potassium hydroxide, lithium hydroxide, magnesium hydroxide, and calcium hydroxide, and at least one inert solvent, e.g., methanol, ethanol, propanol and the like. In embodiments, the compound of formula V may be combined with sodium hydroxide and methanol to produce the compound of formula I.

In embodiments, the first process provides conversion of a monosubstituted urea to a disubstituted aminouracil, and specifically a 1,3-disubstituted 6-aminouracil, without need for further purification.

In embodiments, the disubstituted aminouracil illustrated in the compound of formula I may be further processed to produce selective xanthine and/or xanthine-related compounds which also do not require further purification. Examples of xanthine and/or xanthine-related compounds may be found, e.g., in U.S. Pat. No. 7,342,006 incorporated herein by reference in its entirety.

In embodiments, the first process may include additional steps:
e) reacting the compound of formula I with a nitration agent to produce the compound of formula VI,

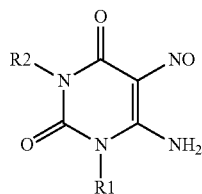

VI f) reacting the compound of formula VI with a first acylating agent of the formula R'—CO—W' to produce the compound of formula VII, and,

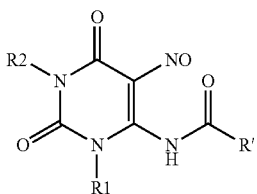

VII wherein W' is a leaving group, g) reacting the compound of formula VII with a reducing agent followed by ring cyclization in an aprotic solvent to produce the xanthine compound of formula VIII.

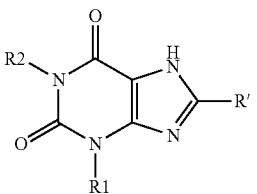

VIII

In embodiments involving step e) of the first process, the nitration agent is, e.g., $NaNO_2/AcOH$, $HNO_3/H_2SO_4$, $N_2O_5/P_2O_5/CCl_4$, HONO, $EtONO_2$, $CH_3COONO_2$ and $NO_2^+ CF_3SO_3^-$. In embodiments, the nitration agent includes $NaNO_2/AcOH$.

In embodiments involving step g) of the first process, the reducing agent is, e.g., hydrogen and palladium on carbon, or sodium dithionite. In embodiments the reducing agent includes sodium dithionite and an aprotic solvent such as dimethyl sulfoxide, acetonitrile, acetone, dimethylformamide, ethyl acetate, tetrahydrofuran, dichloromethane or combinations thereof. In embodiments involving step g) of the first process, the reducing agent includes sodium dithionite and the aprotic solvent includes dimethyl sulfoxide.

In embodiments, in addition to steps (a)-(e), the first process may further include the additional steps of: h) reacting the compound of formula VI with a reducing agent to produce the compound of formula XIV,

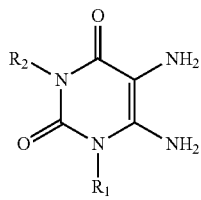

XIV i) reacting the compound of formula XIV with a first acylating agent of the formula R'—CO—W' to produce the compound of formula XV, and,

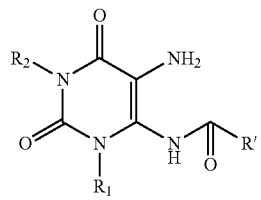

XV wherein R' is as described hereinbelow and W' is a leaving group, j) reacting the compound of formula XV with a metal hydroxide to produce the compound of formula VIII.

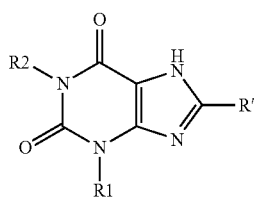

VIII

Optionally, in addition to steps (h)-(j), the first process may further include the following step:

k) reacting the compound of formula VIII with a second acylating agent of the formula R"—CO—W" to produce the compound of formula XVI.

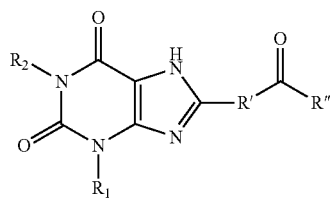

XVI wherein R" is as described hereinbelow, and W'" is a leaving group.

In embodiments, the first and second acylating agents may be the same and/or different. In embodiments, R' and R" may be the same or different compounds. In embodiments, W, W' and W'" may the same or different leaving groups. In embodiments, R' may include a primary or secondary amine.

In embodiments wherein the first process further includes step (k), R' may be selected from the group consisting of:

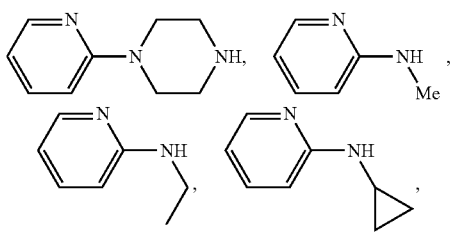

-continued

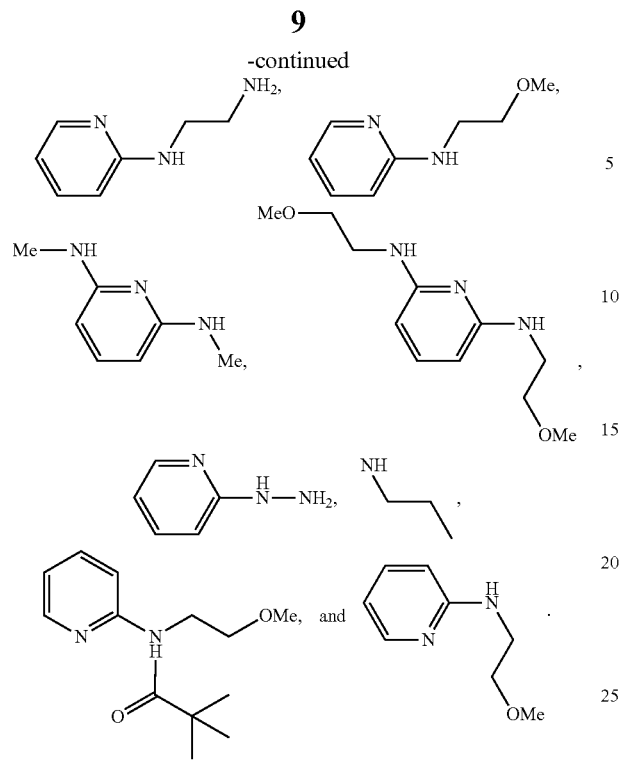

In embodiments wherein the first process further includes step (k), R" may be selected from the group consisting of:

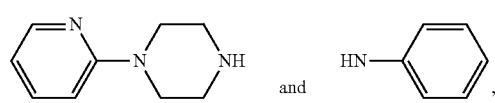

In embodiments wherein the first process further includes step (k), R' and R" may be selected from the following pairs:

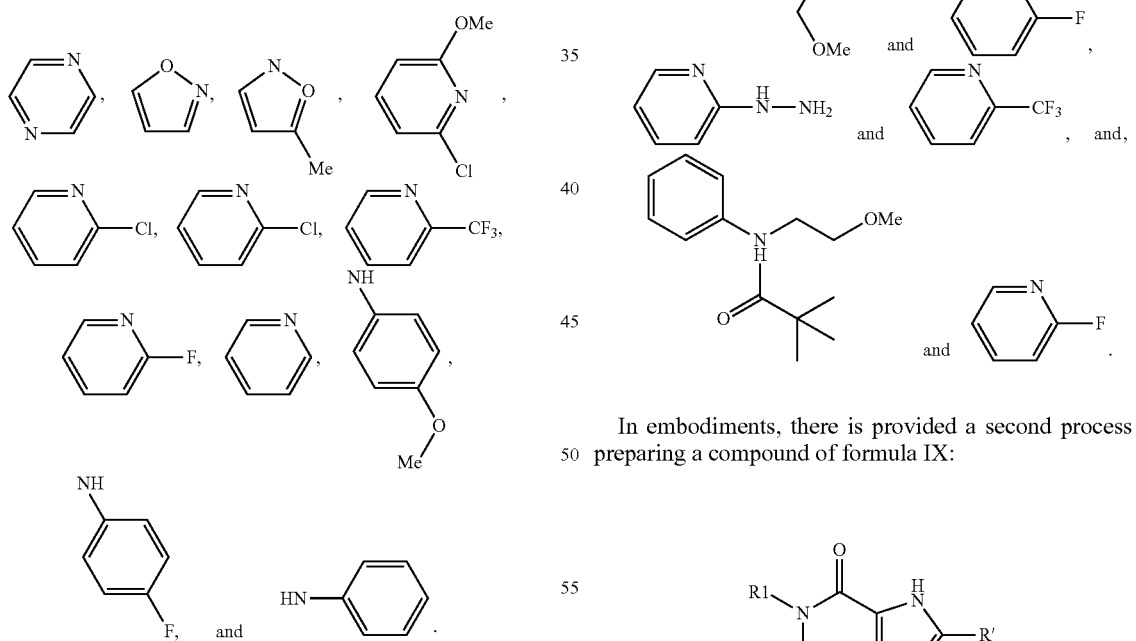

In embodiments, there is provided a second process for preparing a compound of formula IX:

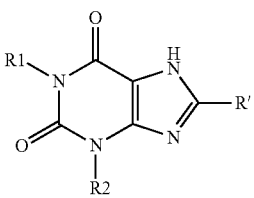

IX wherein:

$R^1$ and $R^2$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10})$ aryl, $(C_6-C_{10})$aryl$(C_1-C_8)$alkyl-, $(C_5-C_{10})$heteroaryl, or $(C_5-C_{10})$heteroaryl$(C_1-C_8)$alkyl-;

R' is hydrogen, halogen, substituted or unsubstituted $(C_1-C_8)$alkyl, $(C_3-C_8)$alkenyl, $(C_3-C_8)$alkynyl, $(C_1-C_8)$ alkoxy, $(C_3-C_8)$cyclo alkyl, $(C_3-C_8)$cycloalkyl$(C_1-C_8)$ alkyl-, $(C_4-C_{10})$heterocycle, $(C_4-C_{10})$heterocycle$(C_1-C_8)$alkyl-, $(C_6-C_{10})$aryl, $(C_6-C_{10})$aryl$(C_1-C_8)$alkyl-, $(C_5-C_{10})$hetero aryl, $(C_5-C_{10})$heteroaryl$(C_1-C_8)$alkyl-, or —X$(Z^1)_n$—Z;

X is a 5-10 member heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine —N(R$^9$)— groups;

Z is —OR$^3$, —SR$^3$, halo, —S(O)$_m$—NR$^4$R$^5$, —NR$^4$R$^5$, or $(C_4-C_{10})$heterocycle wherein the heterocycle is optionally substituted with 1, 2, 3, or 4 substituents independently selected from halo, cyano, nitro, —OR$^a$, —SR$^a$, $(C_1-C_8)$alkyl, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

each Z$^1$ is independently $(C_1-C_8)$alkyl, $(C_2-C_8)$alkenyl, $(C_2-C_8)$alkynyl, —OR$^6$, —SR$^6$, halo, R$^6$O$(C_1-C_8)$alkyl, R$^7$R$^8$N$(C_1-C_8)$alkyl, halo$(C_1-C_8)$alkyl, —NR$^7$R$^8$, R$^7$R$^8$N$(C_1-C_8)$alkyl, —C(O)R$^6$, —COOR$^6$, and —C(O)NR$^7$R$^8$;

R$^3$ is $(C_1-C_8)$alkyl, $(C_3-C_8)$alkenyl, $(C_3-C_8)$alkynyl, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —C(O)R$^6$, or C(O)NR$^7$R$^8$;

R$^4$ and R$^5$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_6-C_{18})$polycycloalkyl, $(C_6-C_{18})$polycycloalkyl$(C_1-C_8)$alkyl-, $(C_3-C_{10})$heterocycle, $(C_3-C_{10})$heterocycle$(C_1-C_8)$alkyl —NR$^7$R$^8$, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —(C$_2$-C$_4$—Y)$_q$—(CH$_2$)$_{2-4}$—X$^1$, C(O)R$^6$, —CO$_2$R$^6$, —C(O)NR$^7$R$^8$, or —S(O)$_2$—NR$^7$R$^8$; or R$^4$ and R$^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy (—O—), thio (—S—), sulfinyl (—SO—), sulfonyl (—S(O)$_2$—) and amine —N(R$^9$)— in the ring, wherein the ring is optionally substituted with 1, 2, 3, or 4 substituents independently selected from halo, cyano, nitro, —OR$^a$, —SR$^a$, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and C(O)NR$^b$R$^c$;

X$^1$ is —OR$^6$, —C(O)R$^6$, —CO$_2$R$^6$, or —NR$^7$R$^8$; and Y is oxy (—O—), thio (—S—), sulfinyl (—SO—), sulfonyl (—S(O)$_2$—) and amine —N(R$^9$)—;

wherein the alkyl, alkenyl, cycloalkyl, alkynyl, aryl, heterocycle, or heteroaryl groups of R$^1$, R$^2$, R$^3$, R$^4$ and R$^5$ groups are optionally substituted with one or more substituents independently selected from halo, cyano, nitro, —OR$^a$, —SR$^a$, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

wherein R$^6$ is hydrogen, $(C_1-C_8)$alkyl, R$^a$O$(C_1-C_8)$alkyl, R$^b$R$^c$N$(C_1-C_8)$alkyl, halo$(C_1-C_8)$alkyl, $(C_3-C_{10})$heterocycle, $(C_3-C_{10})$heterocycle$(C_1-C_8)$alkyl-, $(C_6-C_{10})$aryl, $(C_6-C_{10})$aryl$(C_1-C_8)$alkyl-, $(C_4-C_{10})$hetero aryl, $(C_4-C_{10})$heteroaryl$(C_1-C_8)$alkyl-; wherein the heterocycle, heteroaryl or aryl are optionally substituted with 1, 2, 3, or 4 substituents independently selected from halo, cyano, nitro, —OR$^a$, SR$^a$, $(C_6-C_{10})$aryl —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, C(O)R$^a$, —COOR$^a$, and —C(O)NR$^b$R$^c$;

wherein R$^7$, R$^8$ and R$^9$ are independently hydrogen, $(C_1-C_8)$alkyl, R$^a$O$(C_1-C_8)$alkyl, R$^b$R$^c$N$(C_1-C_8)$alkyl, halo$(C_1-C_8)$alkyl, $(C_3-C_{10})$hetero cycle, $(C_6-C_{10})$aryl, $(C_6-C_{10})$aryl$(C_1-C_8)$alkyl-, $(C_4-C_{10})$heteroaryl; —COOR$^a$, —C(O)R$^a$, or —C(O)NR$^b$R$^c$ wherein the heterocycle, heteroaryl or aryl are optionally substituted with 1, 2, 3, or 4 substituents independently selected from halo, cyano, nitro, —OR$^a$, —SR$^a$, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and C(O)NR$^b$R$^c$; or R$^7$ and R$^8$ together with the atoms to which they are attached form a saturated or partially unsaturated, mono-, bicyclic- or aromatic ring having 3, 4, 5, 6, 7, or 8, ring atoms optionally ring having from 4 to eight ring atoms and optionally comprising 1, 2, 3, or 4 heteroatoms selected from non-peroxide oxy (—O—), thio (—S—), sulfinyl (—SO—), sulfonyl (—S(O)$_2$—) or amine —N(R$^b$)— in the ring;

R$^a$ is hydrogen, or $(C_1-C_6)$alkyl; R$^b$ and R$^c$ are each independently hydrogen, $(C_1-C_6)$alkyl, $(C_1-C_6)$alkoxy, $(C_3-C_8)$cycloalkyl, $(C_1-C_6)$alkylthio, $(C_6-C_{10})$aryl, $(C_6-C_{10})$aryl$(C_1-C_6)$alkyl-, heteroaryl, or heteroaryl$(C_1-C_6)$ alkyl-; or R$^b$ and R$^c$ together with the nitrogen to which they are attached, form a pyrrolidyl, piperidyl, piperazinyl, azepinyl, diazepinyl, morpholinyl, or thiomorpholinyl ring;

where n is 0, 1, 2, 3, 4, 5, 6, 7, or 8; m is 1, or 2; and q is 1, 2, 3, or 4;

the process including:

a) reacting a monosubstituted urea of formula II

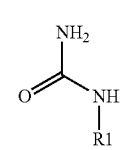

with 3-amino-3-ethoxy-acrylate in the presence of an alkoxide to produce an aminouracil of formula IIIb,

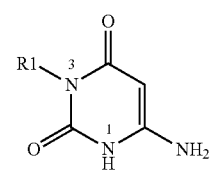

b) reacting the aminouracil of formula IIIb with a nitration agent to produce a compound of formula X,

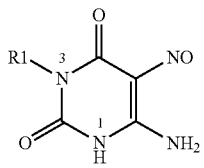

c) reacting the compound of formula X with a reducing agent to produce a compound of formula XI, and,

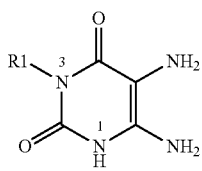

d) reacting the compound of formula XI with an acylating agent of the formula R'—CO—W' to produce a compound of formula XII

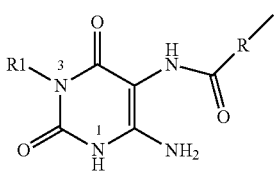

wherein W' is a leaving group, e) reacting the compound of formula XII with a $R^2$-halide, metal carbonate, and an aprotic solvent to produce a compound of formula XIII, and,

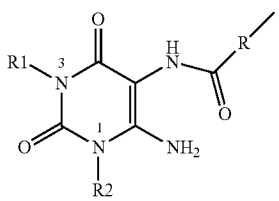

f) reacting the compound of formula XIII with an inert solvent and a metal hydroxide to produce the xanthine compound of formula IX.

In embodiments, the alkoxide of the second process includes at least one metal alkoxide, e.g., sodium ethoxide, potassium ethoxide, calcium ethoxide, potassium tert-butoxide, sodium tert-butoxide, and combinations thereof. In embodiments, the alkoxide includes sodium ethoxide.

In embodiments, the nitration agent of step b) of the second process may include, e.g., $NaNO_2/AcOH$, $HNO_3/H_2SO_4$, $N_2O_5/P_2O_5/CCl_4$, HONO, $EtONO_2$, $CH_3COONO_2$ and $NO_2^+CF_3SO_3^-$. In embodiments, the nitration agent of the second process is $NaNO_2/AcOH$.

In embodiments, the reducing agent of step c) of the second process includes, e.g., hydrogen and palladium on carbon, or sodium dithionite. In embodiments, the reducing agent includes sodium dithionite and an aprotic solvent such as dimethyl sulfoxide, acetonitrile, acetone, dimethylformamide, ethyl acetate, tetrahydrofuran, dichloromethane and combinations thereof. In embodiments involving step c) of the second process, the reducing agent may be sodium dithionite and the aprotic solvent may be dimethyl sulfoxide.

In embodiments, the compound of formula XII may be combined with $R^2$-halide, a metal carbonate and an aprotic solvent to produce the compound of formula XIII.

Some non-limiting examples of metal carbonates include sodium carbonate, potassium carbonate, lithium carbonate, cesium carbonate, sodium bicarbonate, potassium bicarbonate, lithium bicarbonate, cesium bicarbonate, and combinations thereof. In embodiments involving the second process, the metal carbonate may be potassium carbonate.

Some non-limiting examples of aprotic solvents include dimethyl sulfoxide, acetonitrile, acetone, dimethylformamide, ethyl acetate, tetrahydrofuran, dichloromethane, and combinations thereof. In embodiments, the aprotic solvent of step e) of the second process includes dimethylformamide.

In embodiments, the compound of formula XII may be combined with a $R^2$-halide, dimethylformamide and potassium carbonate to produce the compound of formula XIII.

In embodiments, the compound of formula XIII may be combined with at least one metal hydroxide, e.g., sodium hydroxide, potassium hydroxide, lithium hydroxide, magnesium hydroxide, calcium hydroxide, and combinations thereof. In embodiments, the compound of formula XIII may also be combined with at least one inert solvent such as methanol, ethanol, propanol and the like. In embodiments, the compound of formula XIII may be combined with sodium hydroxide and methanol to produce the compound of formula IX.

In embodiments, the second process provides conversion of a monosubstituted urea to selective xanthine and/or xanthine-related compounds without need for further purification.

Optionally, in addition to steps (a)-(f), the second process may further include the following step:

g) reacting the compound of formula IX with a second acylating agent of the formula R"—CO—W'" to produce the compound of formula XVII.

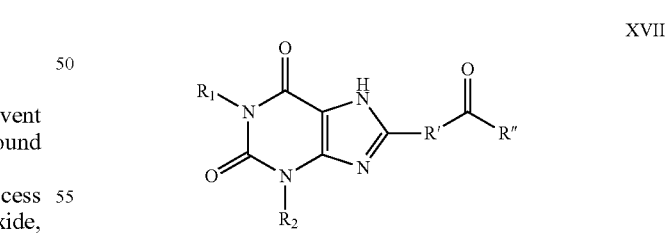

In embodiments wherein the second process includes step (g), the first and second acylating agents may be the same and/or different agent. In embodiments, R' and R" may be the same or different compounds. In embodiments, W, W' and W'" may the same or different leaving groups. In embodiments, R' may include a primary or secondary amine.

In embodiments, wherein the second process further includes step (g), R' may be selected from the group consisting of:

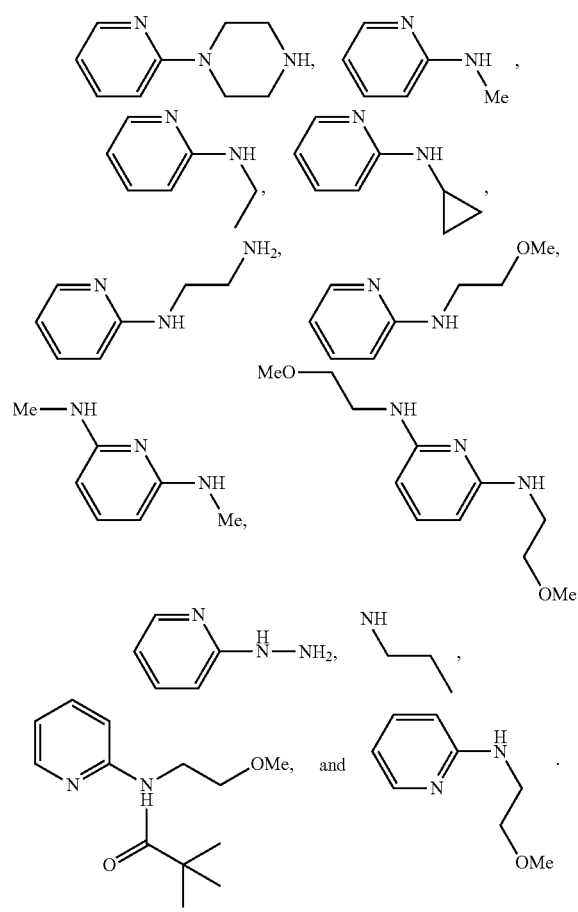

In embodiments wherein the second process further includes step (g), R" may be selected from the group consisting of:

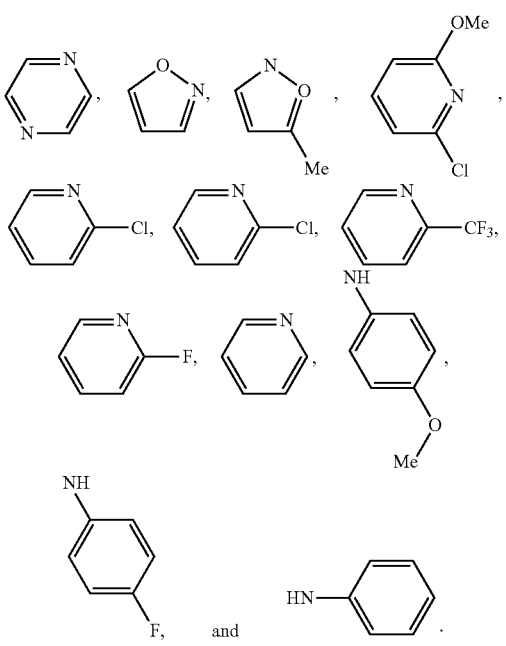

In embodiments wherein the second process further includes step (g), R' and R" may be selected from the following pairs:

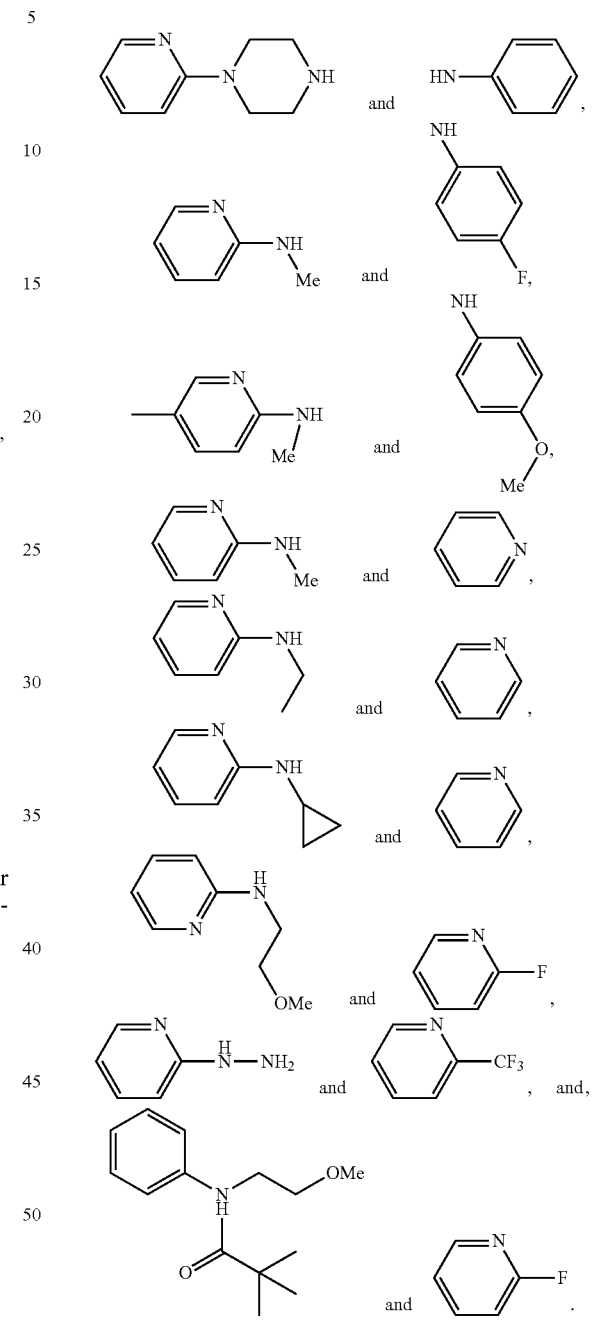

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

"Aryl" denotes a phenyl radical or an ortho-fused bicyclic carbocyclic radical having about nine to ten ring atoms in which at least one ring is aromatic.

"Arylalkyl" or "(C$_6$-C$_{10}$)aryl(C$_1$-C$_8$)alkyl-" refer to a group of the formula aryl(C$_1$-C$_8$)alkyl-, where aryl and (C$_1$-C$_8$)alkyl are as defined herein.

"Heterocycle" encompasses a cyclic radical attached or linked via a nitrogen or carbon ring atom of a monocyclic, fused-bicyclic, or bridged-bicyclic, saturated or unsaturated, ring system containing 5-10 ring atoms and preferably from 5-6 ring atoms, consisting of carbon and one, two, three or four heteroatoms each selected from the group consisting of non-peroxide oxy (—O—), thio (—S—), sulfinyl (—SO—), sulfonyl (—S(O)$_2$—), amine —N(R$^9$)—, or —N= groups, wherein R$^9$ is as defined herein, and optionally containing 1-3 double bonds (e.g., —CH=CH— or —CH=N—). Heterocycle includes, for example, tetrahydrofuryl, dihydrofuryl, tetrahydroimidazolyl, azanorbornyl, pyrrolidyl, piperidyl, piperizyl, morpholinyl, azepinyl, 1,3-diazepinyl, 1,3-benzodiazepinyl, 1,4-diazepinyl, 1,4-benzodiazepinyl, 1,5-diazepinyl, 1,5-benzodiazepino and the like.

"Heteroaryl" encompasses a radical attached via a ring atom of a monocyclic aromatic ring containing 5-10 ring atoms, and preferably from 5-6 ring atoms, consisting of carbon and one, two, three or four heteroatoms each selected from the group consisting of non-peroxide oxy (—O—), thio (—S—), sulfinyl (—SO—), sulfonyl (—S(O)$_2$—) or amine (—N(R$^9$)—) groups, wherein R$^9$ is as defined herein. Preferred heteroaryl groups include imidazolyl, triazolyl, triazinyl, oxazoyl, isoxazoyl, thiazolyl, isothiazoyl, thiodiazolyl, pyrrolyl, pyrazinyl, tetrazolyl, pyridinyl, pyrimidinyl, indolyl, isoquinolyl, quinolyl and the like.

"Leaving group" encompasses a molecular fragment that departs with a pair of electrons in heterolytic bond cleavage. Leaving groups can be anions or neutral molecules. Suitable non-limiting examples of anionic or neutral leaving groups include halides such as Cl$^-$, Br$^-$, and I$^-$, sulfonate esters, such as para-toluenesulfonate ("tosylate", TsO$^-$), water (H$_2$O), alcohols (—OH), and ammonia.

As is recognized by one of ordinary skill in the art, the ring(s) of the compounds of the present invention may exist in tautomeric and/or isomeric forms or as tautomers and/or isomers, and thus are also included within the scope of the invention. For example, isomers are represented as the structures (formula IIIa) and (formula IIIb):

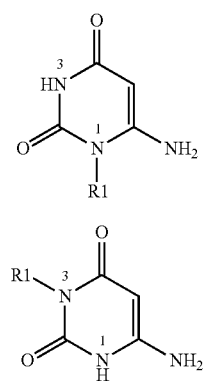

By naming or referring to one compound (III), for example, it is understood for the purposes of the present application that the isomers (IIIa) and (IIIb) are also intended. Similarly, by referring to compound (IIIa), it is understood for the purposes of the present application that the isomers (III) and (IIIb) are also intended. The same holds true for references to isomer (IIIb).

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine, for example, anti-tumor activity, herbicidal activity, or other therapeutic activity using the standard tests described herein, or using other similar tests which are well known in the art.

Specific values listed below for radicals, substituents, and ranges, are for illustration only; they may or may not exclude other defined values or other values within defined ranges for the radicals and substituents.

Some non-limiting examples of: (C$_1$-C$_8$)alkyl can include methyl, ethyl, n-propyl, isopropyl, n-butyl, iso-butyl, sec-butyl, tert-butyl, n-pentyl, isopentyl, 3-pentyl, n-hexyl, n-heptyl, n-octyl or branched (C$_3$-C$_8$)alkyls; (C$_2$-C$_8$)alkenyl can include vinyl, 1-propenyl, 2-propenyl(allyl), 1-butenyl, 2-butenyl, 3-butenyl, 1-pentenyl, 2-pentenyl, 3-pentenyl, 1-hexenyl, 2-hexenyl, 3-hexenyl, 1-heptenyl, 2-heptenyl, 3-heptenyl, 1-octenyl, 2-octenyl, 3-octenyl, 4-octenyl or branched (C$_3$-C$_8$)alkenyls; (C$_3$-C$_8$)alkenyl can include, 2-propenyl(allyl), 2-butenyl, 3-butenyl, 2-pentenyl, 3-pentenyl, 1-hexenyl, 2-hexenyl, 3-hexenyl, 2-heptenyl, 3-heptenyl, 2-octenyl, 3-octenyl, 4-octenyl, or branched (C$_3$-C$_8$)alkenyls; (C$_2$-C$_8$)alkynyl can include ethynyl, 1-propynyl, 2-propynyl (propargyl), 1-butynyl, 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or branched (C$_3$-C$_8$)alkynyls; (C$_3$-C$_8$) alkynyl can include 2-propynyl(propargyl), 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or branched (C$_3$-C$_8$)alkynyls; (C$_1$-C$_8$)alkoxy can include methoxy, ethoxy, n-propoxy, isopropoxy, n-butoxy, iso-butoxy, sec-butoxy, tert-butoxy, pentoxy, 3-pentoxy, n-hexyloxy, n-heptyloxy, n-octyloxy, or branched (C$_3$-C$_8$)alkoxys; halo(C$_1$-C$_8$)alkyl can include iodomethyl, bromomethyl, chloromethyl, fluoromethyl, trifluoromethyl, 2-chloroethyl, 2-bromoethyl, 2-fluoroethyl, 3-fluoropropyl, 2,2,2-trifluoroethyl, pentafluoroethyl, or branched halo(C$_3$-C$_8$)alkyls; (C$_3$-C$_8$)cycloalkyl can include cyclopropyl, cyclobutyl, cyclopentyl, cyclohexyl, cycloheptyl or cyclooctyl; (C$_3$-C$_8$)cycloalkyl(C$_1$-C$_8$)alkyl- can include cyclopropylmethyl, cyclobutylmethyl, cyclopentylmethyl, cyclohexylmethyl, 2-cyclopropylethyl, 2-cyclobutylethyl, 2-cyclopentylethyl or 2-cyclohexylethyl; $(C_6-C_{10})$aryl can include phenyl, indenyl or naphthyl; Heterocycle can include tetrahydrofuryl, dihydrofuryl, tetrahydroimidazolyl, azanorbornyl, pyrrolidyl, piperidyl, piperizyl, morpholinyl, azepinyl, 1,3-diazepinyl, 1,3-benzodiazepinyl, 1,4-diazepinyl 1,4-benzodiazepinyl, 1,5-diazepinyl, or 1,5-benzodiazepino.

Some non-limiting examples of arylalkyl can include phenylethyl, benzyl, 2-phenylpropyl, 3-phenylpropyl, 2-naphthylmethyl or 3-naphthylmethyl; and heteroaryl can include imidazolyl, triazolyl, triazinyl, oxazoyl, isoxazoyl, thiazolyl, isothiazoyl, pyrrolyl, pyrazinyl, tetrazolyl, pyridyl, pyrimidinyl, indolyl, isoquinolyl, quinolyl, or an oxide thereof.

The $(C_1-C_8)$alkyl groups can be methyl, ethyl, propyl, butyl, pentyl, hexyl, heptyl, and octyl; alkenyl groups are ethenyl, propenyl, butenyl, pentenyl, and hexenyl.

In embodiments, W is a halogen.
In embodiments, W is chloride.
In embodiments, W is an alcohol.
In embodiments, W' is a halogen.
In embodiments, W' is chloride.
In embodiments, W' is an alcohol.
In embodiments, W" is a halogen.
In embodiments, W" is chloride.
In embodiments, W" is an alcohol.
In embodiments, $R^1$ is hydrogen, $(C_1-C_4)$alkyl, $(C_3-C_4)$alkenyl, $(C_3-C_4)$alkynyl, phenyl, or phenyl$(C_1-C_4)$alkyl.
In embodiments, $R^1$ is $(C_3-C_6)$cycloalkyl or $(C_3-C_6)$cycloalkyl$(C_1-C_4)$alkyl.
In embodiments, $R^1$ includes cyclopropyl or cyclopropylmethyl.
In embodiments, $R^1$ is hydrogen, methyl, ethyl, allyl, propargyl, i-propyl, n-propyl, n-butyl, i-butyl, phenyl, phenethyl, or benzyl.
In embodiments, $R^1$ is hydrogen, methyl, ethyl, allyl, propargyl, i-propyl, n-propyl, or (methoxyphenyl)ethyl.
In embodiments, $R^1$ includes propyl or cyclopropyl.
In embodiments, $R^2$ is hydrogen, $(C_1-C_4)$alkyl, $(C_3-C_4)$alkenyl, $(C_3-C_4)$alkynyl, phenyl, or phenyl$(C_1-C_4)$alkyl.
In embodiments, $R^2$ is $(C_3-C_6)$cycloalkyl and $(C_3-C_6)$cycloalkyl$(C_1-C_4)$alkyl-.
In embodiments, $R^2$ is cyclopropyl or cyclopropylmethyl.
In embodiments, $R^2$ is hydrogen, methyl, ethyl, allyl, propargyl, i-propyl, n-propyl, n-butyl, i-butyl, phenyl, phenethyl, or benzyl.
In embodiments, $R^2$ is hydrogen, methyl, ethyl, allyl, propargyl, i-propyl, n-propyl, or (methoxyphenyl)ethyl.
In embodiments, $R^2$ is propyl or cyclopropyl.
In embodiments, R' is $(C_3-C_6)$cycloalkyl and $(C_3-C_6)$cycloalkyl$(C_1-C_4)$alkyl-.
In embodiments, R' is cyclopropyl or cyclopropylmethyl.
In embodiments, R' is hydrogen, $(C_1-C_4)$alkyl, $(C_3-C_4)$alkenyl, $(C_3-C_4)$alkynyl, phenyl, or phenyl$(C_1-C_4)$alkyl.
In embodiments, R' is $X(Z^1)_n$—Z.
In embodiments, X is imidazolyl, triazolyl, triazinyl, oxazoyl, isoxazoyl, thiazolyl, isothiazoyl, thiodiazoyl, pyrrolyl, pyrazinyl, tetrazolyl, pyridinyl, pyrimidinyl, indolyl, isoquinolyl, or quinolyl, each optionally substituted with 1, 2, or 3 substituents independently selected from halo, cyano, nitro, $(C_1-C_8)$alkyl, —$OR^a$, $SR^a$, $(C_6-C_{10})$aryl, —$O(C_6-C_{10})$aryl, hydroxy$(C_1-C_8)$alkyl, $R^bR^cN(C_1-C_8)$alkyl, halo$(C_1-C_8)$alkyl, —$NR^bR^c$, —$C(O)R^a$, —$COOR^a$, and $C(O)NR^bR^c$.
In embodiments, X is 2-pyridinyl, 3-pyridinyl, or 4-pyridinyl, each optionally substituted with 1, 2, or 3 substituents independently selected from halo, cyano, nitro, $(C_1-C_8)$alkyl, $OR^a$, $SR^a$, $(C_6-C_{10})$aryl, —$O(C_6-C_{10})$aryl, hydroxy$(C_1-C_8)$alkyl, $R^bR^cN(C_1-C_8)$alkyl, halo$(C_1-C_8)$alkyl, —$NR^bR^c$, —$C(O)R^a$, —$COOR^a$, and —$C(O)NR^bR^c$.

In embodiments, Z is —OH, —$O(C_1-C_4)$alkyl, —$O(C_6-C_{10})$aryl, —$O(C_6-C_{10})$aryl$(C_1-C_4)$alkyl, —$NR^4R^5$, F, Cl, Br, or I.

In embodiments, Z is —$NR^4R^5$.

In embodiments, $X(Z^1)_n$—Z includes

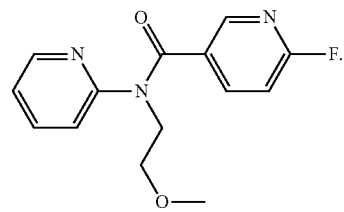 [SMILES: COCCN(C(=O)c1ccc(F)nc1)c1ccccn1]

In embodiments, the processes described herein may be used to form xanthine and/or xanthine-related compounds, some non-limiting examples include:

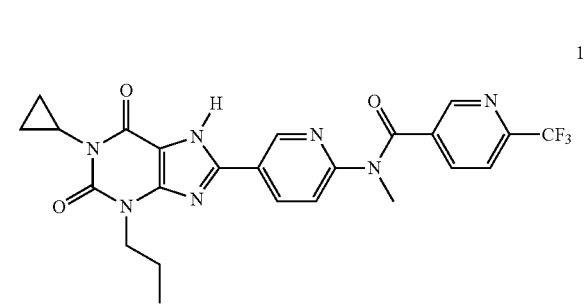

1

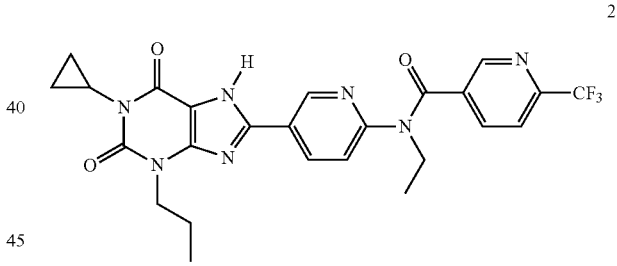

2

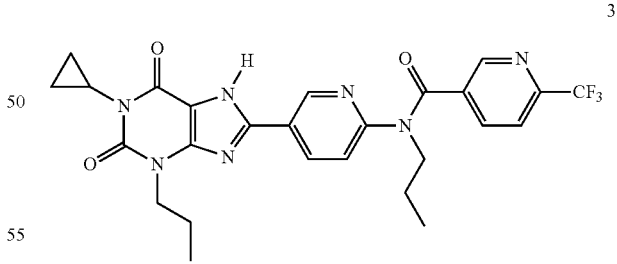

3

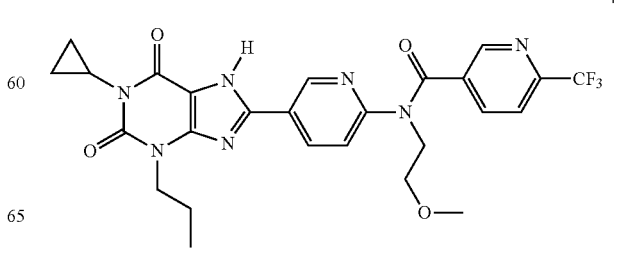

4

-continued
5
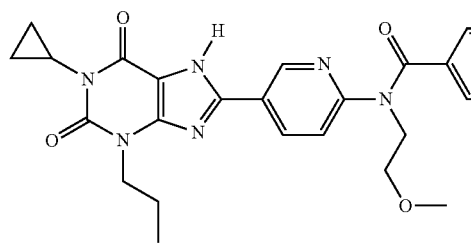
6
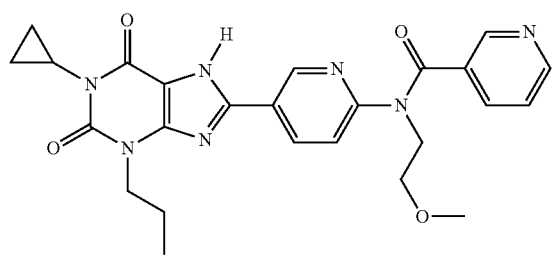
7
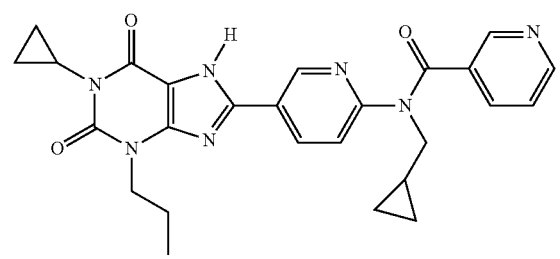
8
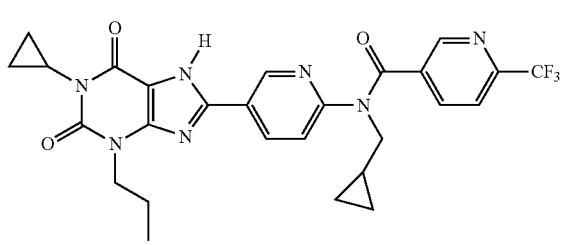
9
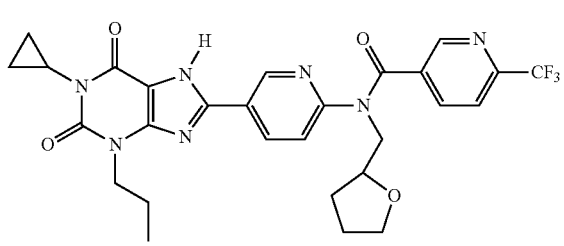
10
-continued
11
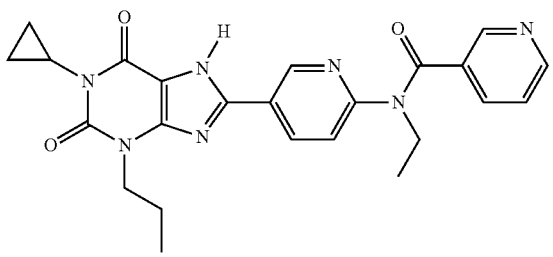
12
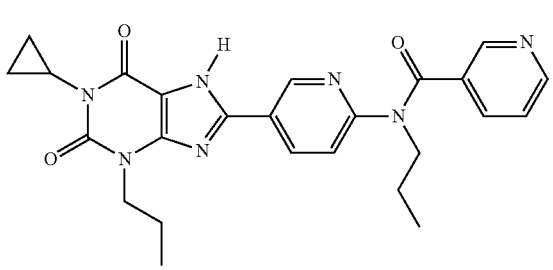
13
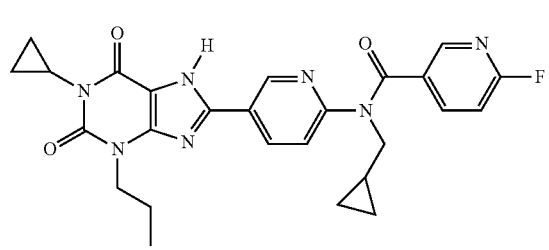
14
15
16
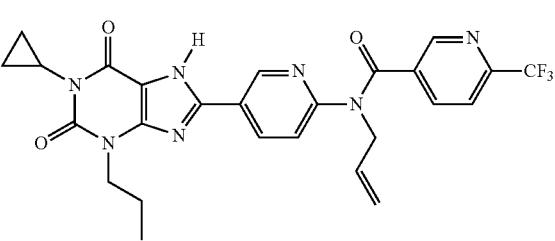

-continued
17
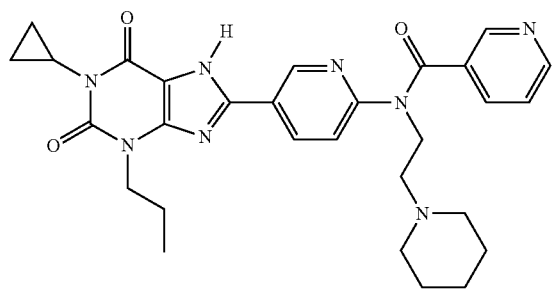
18
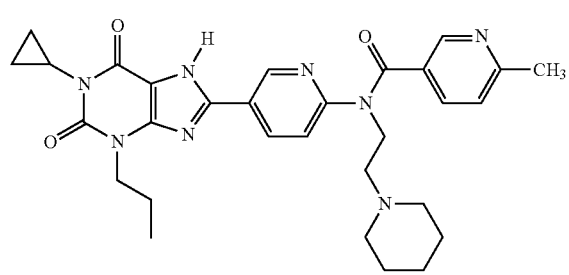
19
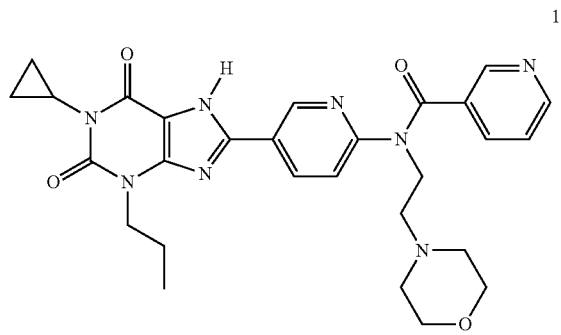
20
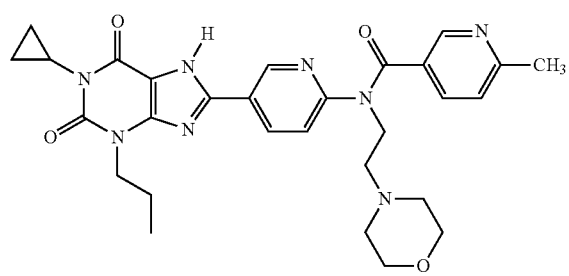
21
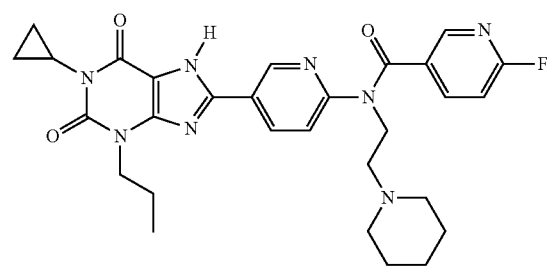
-continued
22
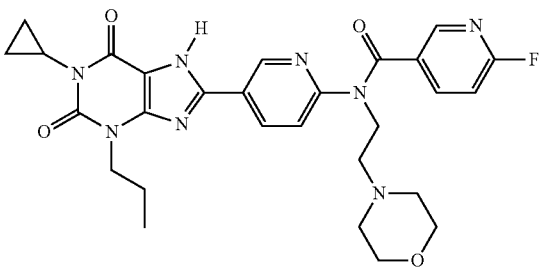
23
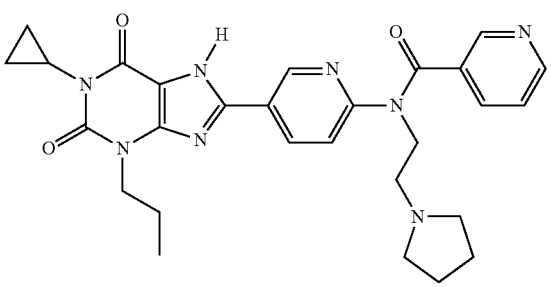
24
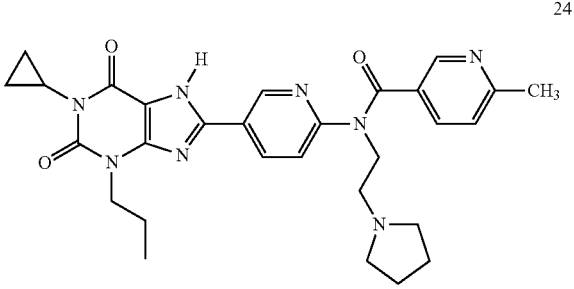
25
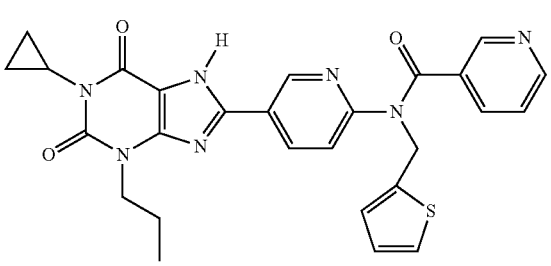
26
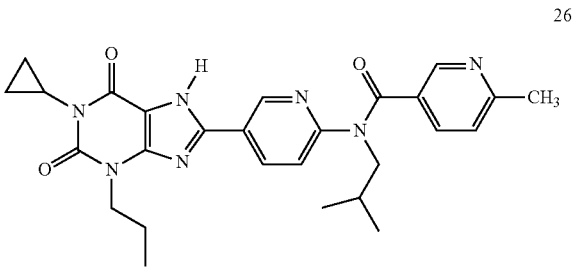

27

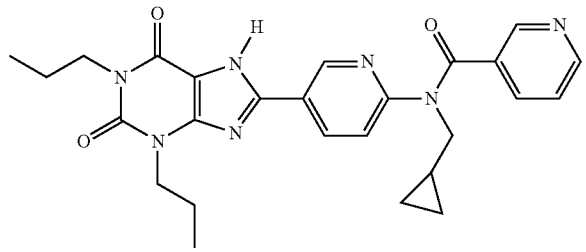

28

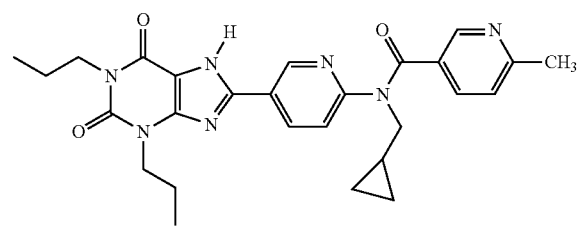

In embodiments the process described herein may prepare compounds of the formulas XVI or XVII

XVI

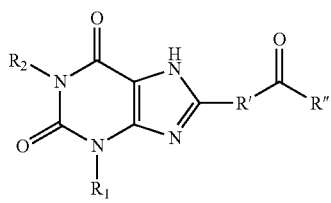

XVII

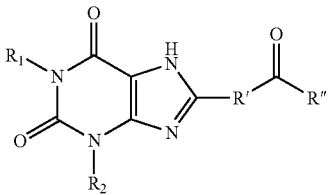

wherein:
$R^1$ and $R^2$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10})$aryl, $(C_6-C_{10})$aryl$(C_1-C_8)$alkyl-, $(C_5-C_{10})$heteroaryl, or $(C_5-C_{10})$heteroaryl$(C_1-C_8)$alkyl-;

R' and R" are independently hydrogen, halogen, substituted or unsubstituted $(C_1-C_8)$alkyl, $(C_3-C_8)$alkenyl, $(C_3-C_8)$alkynyl, $(C_1-C_8)$alkoxy, $(C_3-C_8)$cyclo alkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10}$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, or —X$(Z^1)_n$—Z;

X is a 5-10 member heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine —N(R$^9$)— groups;

Z is —OR$^3$, —SR$^3$, halo, —S(O)$_m$—NR$^4$R$^5$, —NR$^4$R$^5$, or $(C_4-C_{10})$heterocycle wherein the heterocycle is optionally substituted with 1, 2, 3, or 4 substituents independently selected from halo, cyano, nitro, —OR$^a$, —SR$^a$, $(C_1-C_8)$alkyl, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

each $Z^1$ is independently $(C_1-C_8)$alkyl, $(C_2-C_8)$alkenyl, $(C_2-C_8)$alkynyl, —OR$^6$, —SR$^6$, halo, R$^{60}$$(C_1-C_8)$alkyl, R$^7$R$^8$N$(C_1-C_8)$alkyl, halo$(C_1-C_8)$alkyl, —NR$^7$R$^8$, R$^7$R$^8$N$(C_1-C_8)$alkyl, —C(O)R$^6$, —COOR$^6$, and —C(O)NR$^7$R$^8$;

$R^3$ is $(C_1-C_8)$alkyl, $(C_3-C_8)$alkenyl, $(C_3-C_8)$alkynyl, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —C(O)R$^6$, or —C(O)NR$^7$R$^8$;

$R^4$ and $R^5$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_6-C_{18})$polycycloalkyl, $(C_6-C_{18})$polycycloalkyl$(C_1-C_8)$alkyl-, $(C_3-C_{10})$heterocycle, $(C_3-C_{10})$heterocycle$(C_1-C_8)$alkyl —NR$^7$R$^8$, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —(C$_2$-C$_4$—Y)$_q$—(CH$_2$)$_{2-4}$—X$^1$, —C(O)R$^6$, —CO$_2$R$^6$, —C(O)NR$^7$R$^8$, or —S(O)$_2$—NR$^7$R$^8$; or $R^4$ and $R^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy (—O—), thio (—S—), sulfinyl (—SO—), sulfonyl (—S(O)$_2$—) and amine —N(R$^9$)— in the ring, wherein the ring is optionally substituted with 1, 2, 3, or 4 substituents independently selected from halo, cyano, nitro, —OR$^a$, —SR$^a$, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

$X^1$ is —OR$^6$, —C(O)R$^6$, —CO$_2$R$^6$, or —NR$^7$R$^8$; and Y is oxy (—O—), thio (—S—), sulfinyl (—SO—), sulfonyl (—S(O)$_2$—) and amine —N(R$^9$)—;

wherein the alkyl, alkenyl, cycloalkyl, alkynyl, aryl, heterocycle, or heteroaryl groups of $R^1$, $R^2$, $R^3$, $R^4$ and $R^5$ groups are optionally substituted with one or more substituents independently selected from halo, cyano, nitro, —OR$^a$, —SR$^a$, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

wherein $R^6$ is hydrogen, $(C_1-C_8)$alkyl, R$^a$O$(C_1-C_8)$alkyl, R$^b$R$^c$N$(C_1-C_8)$alkyl, halo$(C_1-C_8)$alkyl, $(C_3-C_{10})$heterocycle, $(C_3-C_{10})$heterocycle$(C_1-C_8)$alkyl-, $(C_6-C_{10})$aryl, $(C_6-C_{10})$aryl$(C_1-C_8)$alkyl-, $(C_4-C_{10})$hetero aryl, $(C_4-C_{10})$heteroaryl$(C_1-C_8)$alkyl-; wherein the heterocycle, heteroaryl or aryl are optionally substituted with 1, 2, 3, or 4 substituents independently selected from halo, cyano, nitro, —OR$^a$, SR$^a$, $(C_6-C_{10})$aryl —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

wherein $R^7$, $R^8$ and $R^9$ are independently hydrogen, $(C_1-C_8)$alkyl, R$^a$O$(C_1-C_8)$alkyl, R$^b$R$^c$N$(C_1-C_8)$alkyl, halo$(C_1-C_8)$alkyl, $(C_3-C_{10})$hetero cycle, $(C_6-C_{10})$aryl, $(C_6-C_{10})$aryl$(C_1-C_8)$alkyl-, $(C_4-C_{10})$heteroaryl; —COOR$^a$, —C(O)R$^a$, or —C(O)NR$^b$R$^c$ wherein the heterocycle, heteroaryl or aryl are optionally substituted with 1, 2, 3, or 4 substituents independently selected from halo, cyano, nitro, —OR$^a$, —SR$^a$, $(C_6-C_{10})$aryl, —O$(C_6-C_{10})$aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and C(O)NR$^b$R$^c$; or $R^7$ and $R^8$ together with the atoms to which they are attached form a saturated or partially unsaturated, mono-, bicyclic- or aromatic ring having 3, 4, 5, 6, 7, or 8, ring atoms optionally ring having from 4 to eight ring atoms and optionally comprising 1, 2, 3, or 4 heteroatoms selected from non-peroxide oxy (—O—), thio (—S—), sulfinyl (—SO—), sulfonyl (—S(O)$_2$—) or amine —N($R^b$)— in the ring;

$R^a$ is hydrogen, or ($C_1$-$C_6$)alkyl; $R^b$ and $R^c$ are each independently hydrogen, ($C_1$-$C_6$)alkyl, ($C_1$-$C_6$)alkoxy, ($C_3$-$C_8$)cycloalkyl, ($C_1$-$C_6$)alkylthio, ($C_6$-$C_{10}$)aryl, ($C_6$-$C_{10}$)aryl($C_1$-$C_6$)alkyl-, heteroaryl, or heteroaryl($C_1$-$C_6$)alkyl-; or $R^b$ and $R^c$ together with the nitrogen to which they are attached, form a pyrrolidyl, piperidyl, piperazinyl, azepinyl, diazepinyl, morpholinyl, or thiomorpholinyl ring;

where n is 0, 1, 2, 3, 4, 5, 6, 7, or 8; m is 1, or 2; and q is 1, 2, 3, or 4 Turning now to Reaction Schemes A and B provided below, Reaction Scheme A illustrates a general synthetic scheme for the preparation of a 1,3-disubstituted 6-aminouracil and the compound of formula I wherein $R_1$ is propyl and $R_2$ is cyclopropyl. Reaction Scheme B illustrates a general synthetic scheme for the preparation of a xanthine and/or xanthine-related compound of the compound of formula IX wherein $R_1$ is cyclopropyl and $R_2$ is propyl.

REACTION SCHEME A

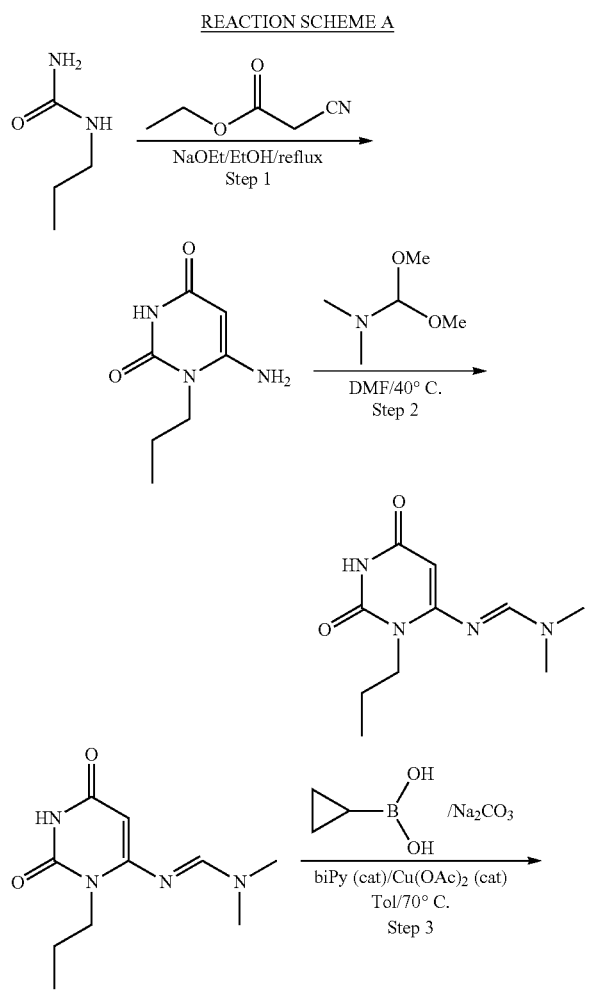

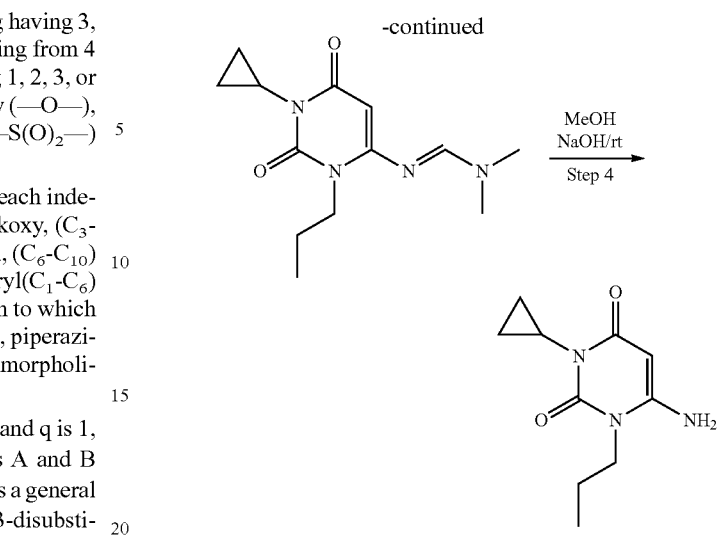

In step 1 of Reaction Scheme A, a 1-substituted 6-aminouracil may be initially produced by the condensation of a monosubstituted urea, i.e., 1-propylurea, with ethyl-2-cyanoacetate in the presence of sodium ethoxide. The sodium ethoxide may be dissolved in a solvent, such as anhydrous ethanol. The condensation reaction may be performed at about 50° C. for about 24 hours or until deemed complete. The residue was dissolved in water and the pH adjusted to about 7 using HCl. The product was collected by filtration, washed with water and dried under vacuum.

In step 2 of Reaction Scheme A, protection of the 1-substituted 6-aminouracil may be performed by suspending the aminouracil in dimethylformamide (DMF) and reacting the suspended aminouracil with DMF-DMA (dimethyl formamide-dimethyl acetal). The protection reaction may occur at a temperature of about 40° C. for about 4 hours or until deemed complete and allowed to cool to about 0° C. for an hour. The protected 1-substituted 6-aminouracil was collected by filtration, washed with MTBE and dried under vacuum overnight.

In step 3 of Reaction Scheme A, alkylation of the 3-position of the protected 1-substituted 6-aminouracil may be performed by reacting the protected aminouracil with cyclopropyl boronic acid, sodium carbonate, copper acetate and bipyridine. Dimethyl carbonate may also be added. The reaction may be performed at about 75° C. and stirred for about 3 hours or until deemed complete. The result may be allowed to cool to about room temperature before being filtered and washed with ethyl acetate. The filtrate may be extracted with a NH$_4$Cl solution and washed again with ethyl acetate. The result may be washed, dried and concentrated under pressure to provide a product capable of being combined with MTBE and heated for about 30 minutes. The product may be allowed to cool to about 0° C. for an hour. The protected 1,3-disubstituted 6-aminouracil was collected by filtration and washed with MTBE.

In step 4 of Reaction Scheme A, deprotection of the protected 1,3-disubstituted 6-aminouracil may occur by reacting the protected 1,3-disubstituted 6-aminouracil with methanol and sodium hydroxide for about 15 hours under stirring until the methanol is evaporated. The reaction may be allowed to cool to about 0° C. for an hour with the addition of water. The 1,3-disubstituted 6-aminouracil was collected by filtration, rinsed with water and dried under vacuum at about 40° C. overnight.

REACTION SCHEME B

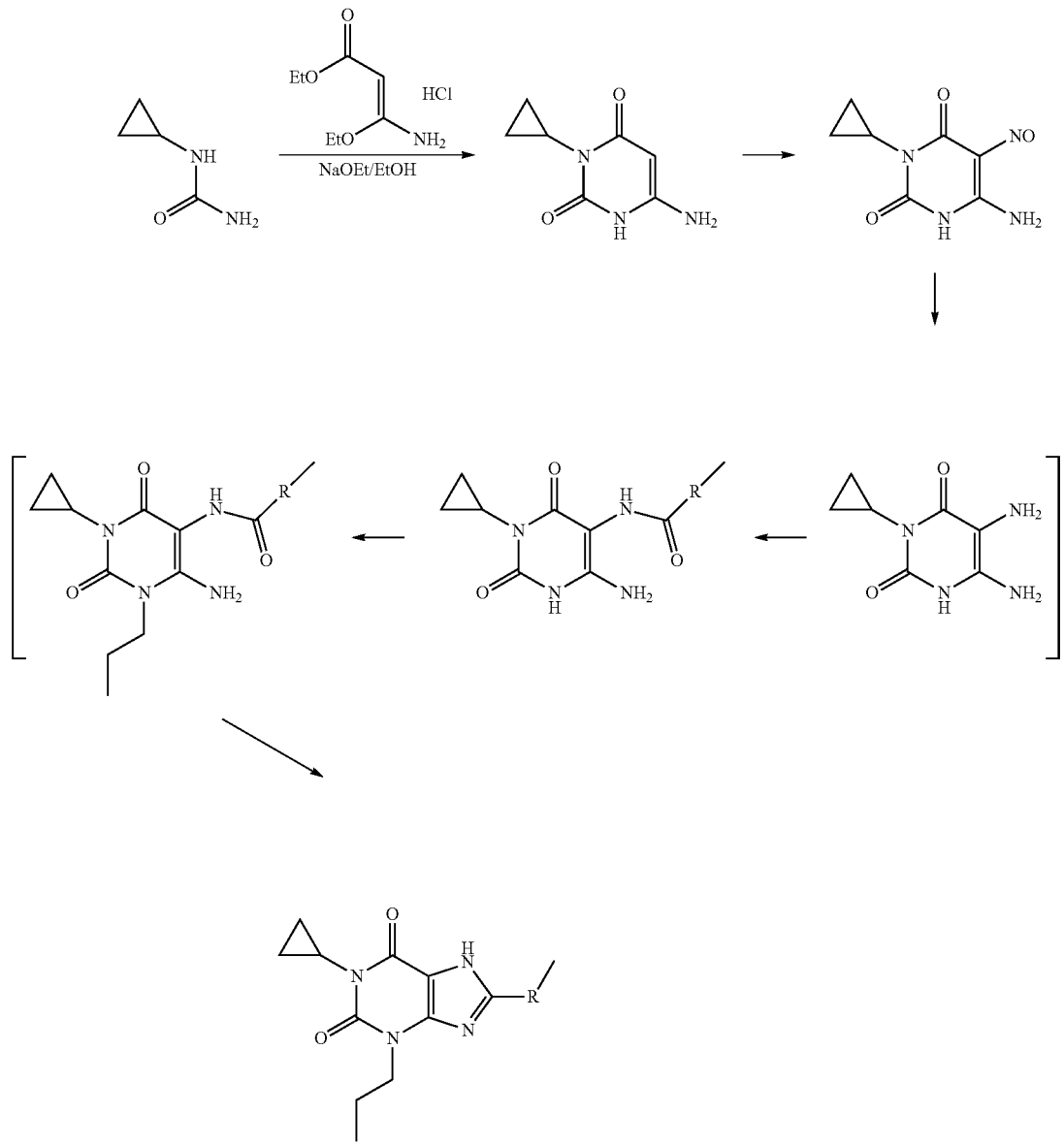

In step 1 of Reaction Scheme B, a 3-substituted 6-aminouracil may be initially produced by the condensation of a monosubstituted urea, i.e., cyclopropylurea, with ethyl-3-amino-3-ethoxyacetate and ethanol. The condensation reaction may be performed at about 75° C. for about 2 hours before the addition of sodium ethoxide and allowed to proceed for about another hour. The ethanol may be evaporated and water added the pH adjusted to about 4-5 using HCl. The product was collected by filtration, washed with water and dried under vacuum overnight.

In step 2 of Reaction Scheme B, nitration of the 3-substituted 6-aminouracil may occur by combining the 3-substituted 6-aminouracil with acetic acid and adding small portions of sodium nitrite over a period of minutes, preferably 10 minutes and stirring. The nitrated 3-substituted 6-aminouracil was collected by filtration, and washed with water.

In step 3 of Reaction Scheme B, a reduction reaction may be performed on the nitrated 3-substituted 6-aminouracil by suspending the nitrated 3-substituted 6-aminouracil in methanol and adding $PtO_2$ and a stream of $H_2$ for about 2 hours. Dichloromethane may be added to dissolve the product and the Pt may be filtered and the methanol removed to yield a 3-substituted 5,6-diaminouracil.

In step 4 of Reaction Scheme B, acylation at the 5-position of the 3-substituted 5,6-diaminouracil may occur by reacting the 3-substituted 5,6-diaminouracil with acyl reagent of a formula R'—CO—W under proper conditions. The 3-substituted 5-acylated 6-aminouracil may be isolated by filtration and collected using techniques known to those skilled in the art.

In step 5 of Reaction Scheme B, the 1-position of the 3-substituted 5-acylated 6-aminouracil may be alkylated by reacting the 3-substituted 5-acylated 6-aminouracil with an alkyl halide, potassium carbonate under mild conditions in DMF. The 1,3-disubstituted, 5-acylated, 6-aminouracil may be isolated by filtration and collected using techniques known to those skilled in the art.

In step 6 of Reaction Scheme B, the 1,3-disubstituted, 5-acylated, 6-aminouracil may be cyclized to produce a xanthine compound. The 1,3-disubstituted, 5-acylated, 6-aminouracil may be cyclized by reacting the 1,3-disubstituted, 5-acylated, 6-aminouracil with a base such as sodium hydroxide and methanol. The resulting xanthine compound may be isolated, filtered and collected using techniques known to those skilled in the art.

EXAMPLE 1

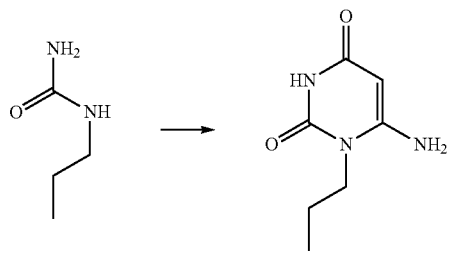

6-Amino-1-propyl-1H-pyrimidine-2,4-dione

Sodium ethoxide (19.99 g, 293.72 mmol, 2 eq) was dissolved in anhydrous ethanol (210 ml) at 50° C. To the solution was added ethyl 2-cyanoacetate (15.67 ml, 146.86 mmol, 1 eq) then 1-propylurea (15 g, 146.86 mmol, 1 eq), and the mixture was stirred at reflux for 24 hours. The solvent was evaporated under reduced pressure, and the residue was dissolved in water (70 ml). The pH of the solution was adjusted to ~7 by using concentrated HCl. The light yellow solid formed was collected by filtration, washed with water, and dried under vacuum to afford 23.82 g of the desired product (96% yield): The desired isomer was determined via 2D-NMR; $^1$H NMR (400 MHz, DMSO-$d_6$) δ 10.3 (1H), 6.79 (2H), 4.52 (1H), 3.68-3.70 (2H), 1.50 (2H), 0.85 (3H); m/z (ES+) 170.18

EXAMPLE 2

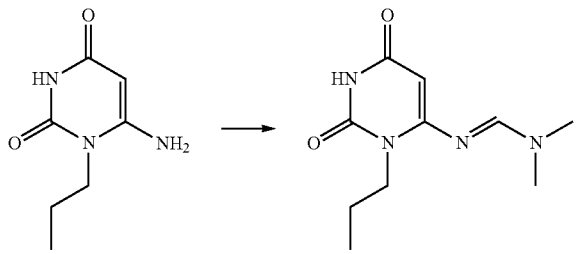 [SMILES: CCCn1c(N)cc(=O)[nH]c1=O ; CCCn1c(/N=C/N(C)C)cc(=O)[nH]c1=O]

N'-(2,6-Dioxo-3-propyl-1,2,3,6-tetrahydro-pyrimidin-4-yl)-N,N-dimethyl-formadidine To a suspension of 6-amino uracil (15 g, 88.66 mmol, 1 eq) in DMF (125 ml) was added DMF-DMA (12.96 ml, 97.53 mmol, 1.1 eq). The mixture was heated at 40° C. for 4 hours. The reaction flask is cooled to 0° C. for 1 hour then collected by filtration and washed with MTBE (50 ml) to afford 18.07 g (91%) after dried under vacuum at 40° C. overnight: $^1$H NMR (400 MHz, DMSO-$d_6$) δ10.58 (1H), 8.05 (1H), 4.96 (1H), 3.8-3.82 (2H), 3.10 (3H), 2.98 (3H), 1.54 (2H), 0.83 (3H); m/z (ES+) 225.26

EXAMPLE 3

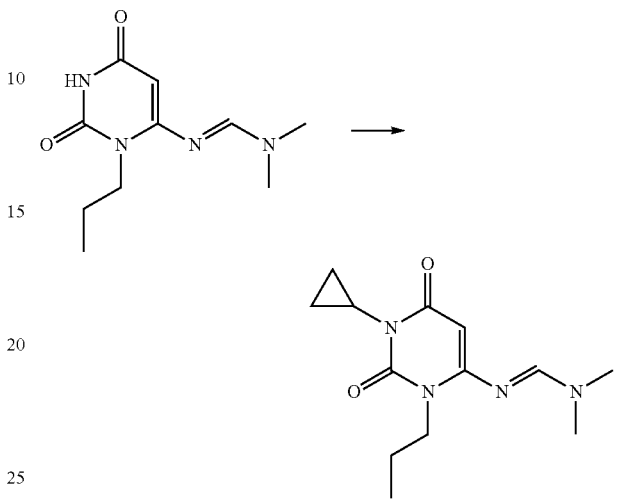

N'-(1-Cyclopropyl-2,6-Dioxo-3-propyl-1,2,3,6-tetrahydro-pyrimidin-4-yl)-N,N-dimethyl-formamidine In a 500 ml 3-necked round bottom flask is charged with protected uracil (15.00 g, 66.89 mmol, 1 eq), cyclopropyl boronic acid (6.90 g, 80.27 mmol, 1.2 eq), sodium carbonate (14.18 g, 133.78 mmol, 2 eq), Cu(OAc)$_2$ (2.43 g, 13.38 mmol, 0.2 eq), and bipyridine (2.09 g, 13.38 mmol, 0.2 eq). Dimethyl carbonate (150 ml) was added. The mixture was warmed to 75° C. and stirred for 3 hours under air (in house air was used; filtered through calcium sulfate cylinder). The resulting mixture was cooled to mom temperature, filtered through Celite pad, and washed with EtOAc (100 ml). The filtrate was extracted with saturated aqueous NH$_4$Cl solution (300 ml); washed the aqueous layer with EtOAc (2×100 ml). The combined organic layers were washed with brine, dried, and concentrated under reduce pressure. To the crude product was added MTBE (150 ml) then heated to reflux for 30 minutes before slowly cooled to 0° C. for 1 hr; product was collected by filtration and washed with MTBE (100 ml) to give product in good yield 14.66 g (83%): $^1$H NMR (400 MHz, DMSO-$d_6$) δ 8.05 (1H), 5.05 (1H), 3.85 (2H), 3.1 (3H), 2.97 (3H), 2.50 (1H), 1.58 (2H), 0.92 (2H), 0.83 (3H), 0.62 (2H); m/z (ES+) 265.33

EXAMPLE 4

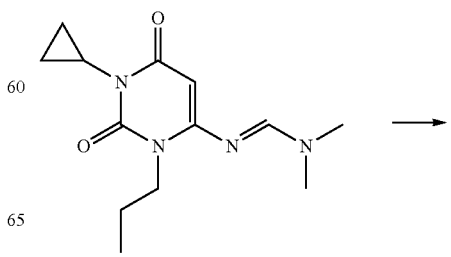

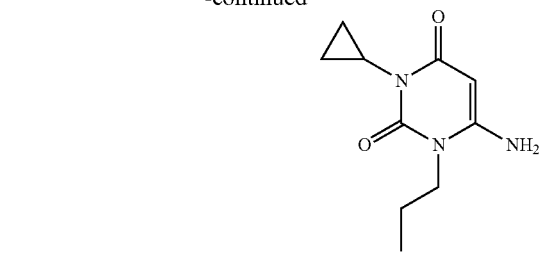

6-Amino-3-cyclopropyl-1-propyl-1H-pyrimidine-2,4-dione

In a 500 ml round bottom flask is charged with N,N-dimethylaminomethylene uracil (15.0 g, 56.75 mmol, 1 eq), followed by methanol (100 ml), and 2N NaOH (56.75 nil, 2 eq). After 15 hours of stirring, methanol was evaporated then cooled to 0° C. for 1 hour with an addition of water (25 nil). Product was filtered, rinsed with cold water, dried under vacuum at 40° C. overnight to give 10.91 g (92%): $^1$H NMR (400 MHz, DMSO-$d_6$) δ 6.72 (2H), 4.59 (1H), 3.70 (2H), 2.45 (1H), 1.50 (2H), 0.85 (5H), 0.59 (2H); m/z (ES+) 210.25

EXAMPLE 5

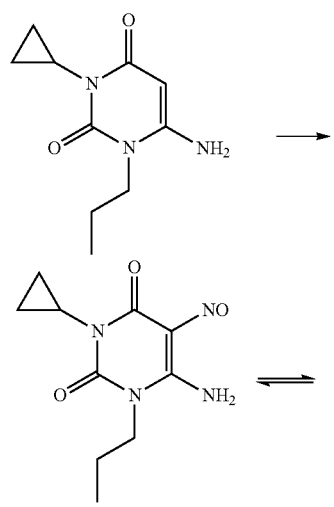

6-Amino-3-cyclopropyl-5-nitroso-1-propyl-1H-pyrimidine-2,4-dione

To a solution of 1-propyl-3-cyclopropyl-6-aminouracils (10 g, 47.85 mmol, 1 eq) in AcOH (31.14 ml, 550.28 mmol, 11.5 eq) and water (9 ml) was added NaNO$_2$ solution (3.71 g, 52.64 mmol, 1.1 eq) in 20 ml of water, and the mixture was stirred at room temperature for 2 hours. Purple solid formed was collected by filtration and washed with cold water to afford compound indicated (8.44 g, 74%) after vacuum dried over night: $^1$H NMR (400 MHz, DMSO-$d_6$) δ 13.25 (1H), 9.08 (1H), 3.75 (2H), 2.65 (1H), 1.50 (2H), 1.02 (2H), 0.86 (3H), 0.75 (2H); m/z (ES+) 239.25

EXAMPLE 6

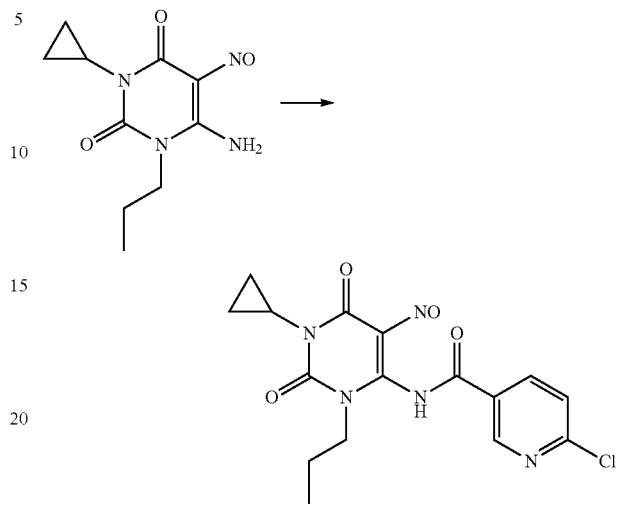

6-Chloro-N-(1-cyclopropyl-5-nitroso-2,6-dioxo-3-propyl-1,2,3,6-tetrahydro-pyrimidin-4-yl)-nicotinamide To a solution of nitroso uracil (5.5 g, 23.1 mmol, 1 eq) in EtOAc (110 ml) was added triethylamine (4.84 ml, 34.65 mmol, 1.5 eq) followed by 6-chloronicotinoyl chloride (4.06 g, 23.1 mmol, 1 eq). The mixture was stirred under nitrogen for two hrs. After that time, the mixture was quenched with water and extracted with EtOAc (2×). The organic phase was dried with anhydrous Na$_2$SO$_4$, filtered and the solvent was removed under reduced pressure, obtaining (8.2 g, 94%, m/z (ES+) 378.8), which was used in the following step without purifying.

EXAMPLE 7

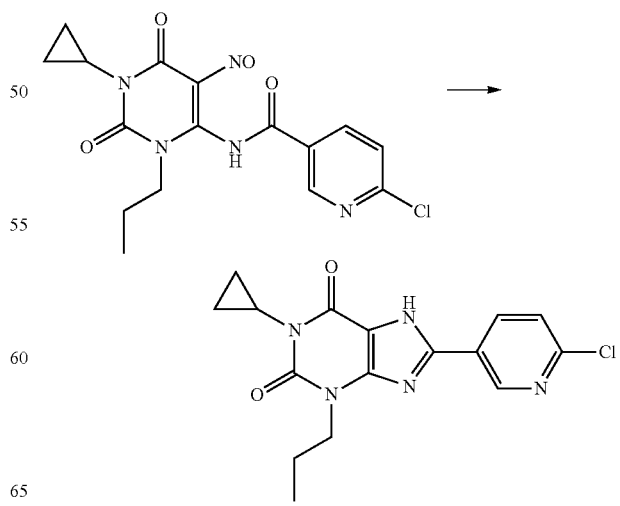

8-(6-Chloro-pyridin-3-yl)-1-cyclopropyl-3-propyl-3,7-dihydro-purine-2,6-dione To a solution of 6-Chloro-N-(1-cyclopropyl-5-nitroso-2,6-dioxo-3-propyl-1,2,3,6-tetrahydro-pyrimidin-4-yl)-nicotinamide (8.2 g, 21.71 mmol, 1 eq) in 60 ml of DMSO was added $Na_2S_2O_4$ (15.11 g, 86.84 mmol, 4 eq). The mixture was stirred at 90° C. for 3 hours. The mixture was quenched with water (50 ml). The resulting precipitate was obtained by filtration and washed with water to give the desired product (5.78 g, 77%) after vacuum dried overnight at 40° C.: $^1$H NMR (400 MHz, DMSO-$d_6$) δ 14.1 (1H), 9.08 (1H), 8.48 (1H), 7.7 (1H), 4.00 (2H), 2.62 (1H), 1.78 (2H), 1.14 (2H), 0.92 (3H), 0.75 (2H); m/z (ES+) 346.79

EXAMPLE 8

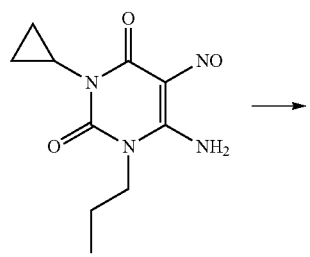

5,6-Diamino-3-cyclopropyl-1-propyl-1,1-pyrimidine-2,4-dione

A solution of sodium dithionite (13.15 g, 75.6 mmol, 6 eq) in $H_2O$ (50 ml) was added to a suspension of 6-Amino-3-cyclopropyl-5-nitroso-1-propyl-1H-pyrimidine-2,4-dione (3 g, 12.6 mmol) in MeOH (50 ml) at room temperature. After stirring for 30 minutes, the precipitate went from purple to white. The reaction mixture was stirred for an additional 2 hours before methanol was evaporate under reduced pressure. The mixture was extracted with EtOAc (2×). The organic phase was dried with anhydrous $Na_2SO_4$, filtered and the solvent was removed under reduced pressure, obtaining (2.49 g, 88%, m/z (ES+) 225.46), which was used in the following step without purifying.

EXAMPLE 9

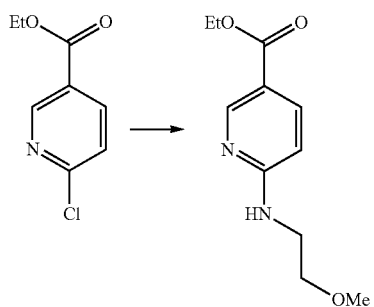 [SMILES: CCOC(=O)c1ccc(Cl)nc1 ; CCOC(=O)c1ccc(NCCOC)nc1]

6-(2-Methoxy-ethylamino)-nicotinic acid ethyl ester 500 ml 3-necked round bottom flask is charged with pyridine chloride (27.69 g, 150 mmol), DMF (200 ml), $K_2CO_3$ (31.05 g, 225 mmol, 1.5 eq), methoxy ethylene amine (16.9 ml, 195 mmol, 1.3 eq) and heated while stirring at 90-95° C. Monitor by HPLC for every 2 hours. Reaction completed after 10 hours. Solid was filtered, washed with toluene (70 ml). The filtrate was extracted with water and back extracted with toluene. The combined organic layers were washed with brine, dried, and concentrated under reduce pressure. Heptane was added to the crude product and stirred for 30 min at 0° C. before filtered and dried to give 22.71 g (67.6%) of clean product: $^1$H NMR (400 MHz, DMSO-$d_6$) δ 8.55 (1H), 7.78 (1H), 7.48 (1H), 6.55 (1H), 4.2 (2H), 3.48 (4H), 3.25 (3H), 1.25 (3H); m/z (ES+) 224.26

EXAMPLE 10

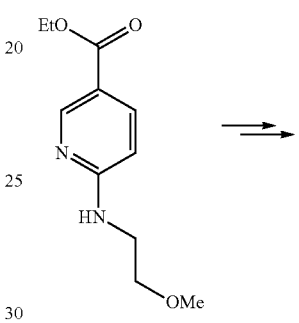

6-[(2,2-Dimethyl propionyl)-(2-methoxy-ethyl)-amino]-nicotinic acid

TEA was added to a solution of 6-(2-Methoxy-ethylamino)-nicotinic acid ethyl ester (3.36 g, 15 mmol) in DCM (55 ml) and cooled to 0° C. PivCl (1.94 ml, 15.75 mmol, 1.05 eq) in DCM (3 ml) was slowly added and the reaction mixture was stirred for 30 min at 0° C. then 2 hours at room temperature. The reaction mixture was poured into 50 ml of water, and aqueous layer was extracted with DCM (3×30 ml). Organic layers were washed with $NaHCO_3$ sat, water and brine, dried over anhydrous $Na_2SO_4$, filtered and the solvent was concentrated under reduced pressure to dryness, obtaining 4.62 g of oily product, which was used in the following step without purifying.

LiOH (1.89 g, 45 mmol, 3 eq) was added to a stirred solution of ester (4.62 g, 15 mmol) in THF/MeOH/Water (30 ml, 15 ml, 7.5 ml) and resulting mixture was stirred at room temperature for 45 min and monitored via HPLC. Reaction mixture was evaporated to dryness and redissolved the rest in 75 ml of water; the solution was acidified to pH 1 with 10% HCl, filtered solid and washed with water. Product was dried in vacuum at 50° C. overnight to obtain 3.52 g (83.2%) of white solid. $^1$H NMR (400 MHz, DMSO-$d_6$) δ 13.4 (1H), 8.89 (1H), 8.32 (1H), 7.5 (1H), 3.8 (2H), 3.45 (2H), 3.18 (3H), 0.98 (9H); m/z (ES+) 280.33

EXAMPLE 11

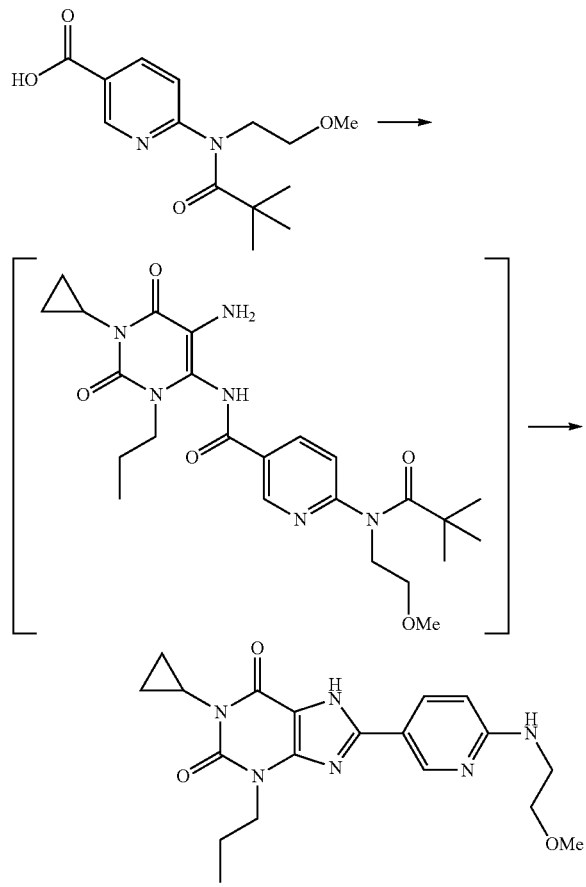

1-Cyclopropyl-8-[6-(2-methoxy-ethylamino)-pyridin-3-yl]-3-propyl-3,7-dihydro-purine-2,6-dione Oxalyl chloride (0.98 ml, 11.25 mmol, 1.05 eq) was added dropwise to a stirred solution of 6-[(2,2-Dimethyl-propionyl)-(2-methoxy-ethyl)-amino]-nicotinic acid (3 g, 10.71 mmol) in DCM (30 Ml) at 0° C. followed by one drop of DMF. Stirred at that temperature for 30 min before the addition of 5,6-Diamino-3-cyclopropyl-1-propyl-1H-pyrimidine-2,4-dione (2.4 g, 10.71 mmol, 1 eq) and followed by pyridine (0.866 ml, 10.71 mmol, 1 eq). The reaction mixture was allowed to warm to room temperature for 3 hr then the mixture was evaporated to dryness and redissolved in 30 ml of 4N NaOH. The reaction mixture was heated to reflux for a total of 5 hours. After cooling to room temperature, the pH adjusted with aqueous hydrochloric acid to 7-8. Water was evaporated to half volume then ethanol was added at 0° C. and stirred overnight (15 hr). The reaction mixture is filtered and the solid was washed with water and then ethanol. The product is then dried at 50° C. to provide 3.41 g (83%). $^1$H NMR (400 MHz, DMSO-$d_6$) δ 13.68 (1H), 8.7 (1H), 8.0 (1H), 7.15 (1H), 6.6 (1H), 3.95 (2H), 3.48 (4H), 3.26 (3H), 2.6 (1H), 1.7 (2H), 1.05 (2H), 0.9 (3H), 0.7 (2H); m/z (ES+) 385.44

EXAMPLE 12

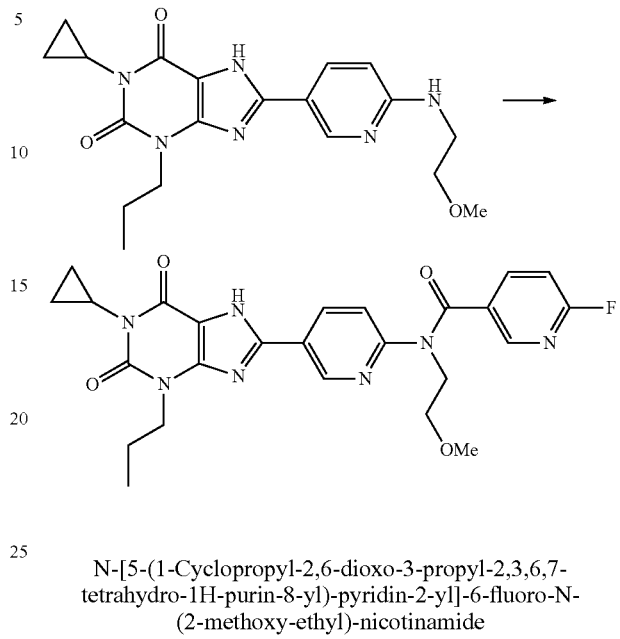

N-[5-(1-Cyclopropyl-2,6-dioxo-3-propyl-2,3,6,7-tetrahydro-1H-purin-8-yl)-pyridin-2-yl]-6-fluoro-N-(2-methoxy-ethyl)-nicotinamide 1-Cyclopropyl-8-[6-(2-methoxy-ethylamino)-pyridin-3-yl]-3-propyl-3,7-dihydro-purine-2,6-dione (2 g, 5.20 mmol) is charged to a reaction flask, followed by anhydrous tetrahydrofuran (25 ml) and N,N-diisopropylethylamine (5 eq). 6-fluoronicotinoyl chloride (1.16 g, 7.28 mmol, 1.4 eq) is added and the mixture is heated to 60° C. It is held for 12 hr and sampled for reaction completion via HPLC: When the reaction is complete, it is cooled to room temperature and water is added then filtered. The filtrate is concentrated then the resulting product is triturated with methanol at 60° C. then cooled to room temperature and filtered. The crude product was again triturated with methanol, filtered and again washed with methanol. The product is then dried at 50° C. to provide 2.41 g (91%). $^1$H NMR (400 MHz, DMSO-$d_6$) δ 13.95 (1H), 8.9 (1H), 8.32 (1H), 8.15 (1H), 7.89 (1H), 7.39 (1H), 7.15 (1H), 4.2 (2H), 3.95 (2H), 3.6 (2H), 3.18 (3H), 2.6 (1H), 1.7 (2H), 1.05 (2H), 0.9 (3H), 0.7 (2H); m/z (ES+) 508.53

EXAMPLE 13

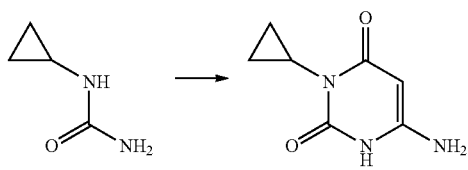 [SMILES: NC(=O)NC1CC1 ; Nc1cc(=O)n(C2CC2)c(=O)[nH]1]

6-Amino-3-cyclopropyl-1H-pyrimidine-2,4-dione

A solution of cyclopropyl urea (10 g, 100 mmol, 1 eq) and ethyl 3-amino-3-ethoxy-acrylate HCl (19.55 g, 100 mmol, 1 eq) in Ethanol (125 ml) was heated at 75° C. for 2 hours. To this solution was added 2 equivalents of NaOEt then heated for an additional one hour. Solvent was evaporated, water (50 ml) was added then acidified via concentrated HCl to pH of 4-5. The resulting precipitate was obtained by filtration and washed with cold water to give the desired product (9.35 g, 56%) after vacuum dried overnight at 40° C.: The desired isomer was determined via 2D-NMR; $^1$H NMR (400 MHz, DMSO-$d_6$) δ 10.18 (1H), 6.10 (2H), 4.44 (1H), 2.38 (1H), 0.85 (2H), 0.62 (2H); m/z (ES+) 168.17

EXAMPLE 14

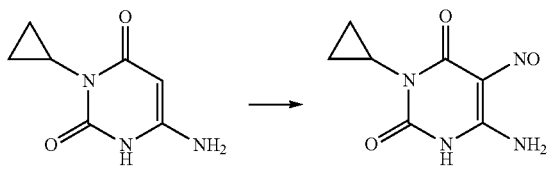

6-Amino-3-cyclopropyl-5-nitrosouracil

To a solution of 6-Amino-3-cyclopropyl-1H-pyrimidine-2,4-dione (5.0 g, 29.9 mmol, 1 eq) in 50% aq AcOH (10 ml) was added $NaNO_2$ (4.13 g, 59.8 mmol, 2 eq) in small portions over a period of 10 min. The mixture was stirred for 1 hr. The purple precipitate was collected by filtration and washed with cold water to give 4.75 g, 81%, m/z (ES+) 197.17), which was used in the following step.

EXAMPLE 15

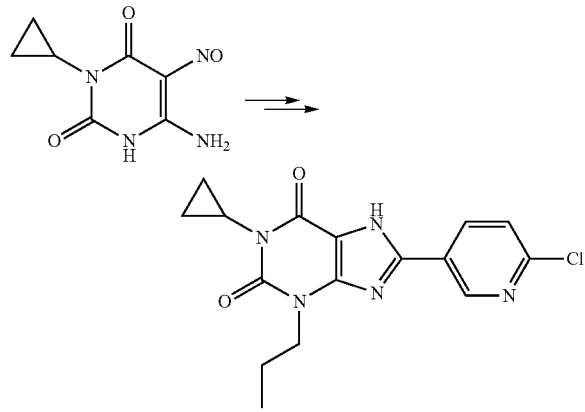

8-(6-Chloro-pyridin-3-yl)-1-cyclopropyl-3-propyl-3,7-dihydro-purine-2,6-dione

6-Amino-3-cyclopropyl-5-nitrosouracrl (4.75 g, 24.21 mmol) was suspended in MeOH (100 ml). $PtO_2$ (0.08 g) was added and a stream of $H_2$ was passed through the suspension. After 2 hr the colored suspension had turned white. $CH_2Cl_2$ (200 ml) was added to dissolve the product. Pt was filtered off and the solvent removed in vacuo to yield the labile diaminouracil (4.29 g, 98%)

To the crude diamine (4.29 g, 23.72 mmol) in EtOAc (50 ml) was added 6-chloronicotinoyl chloride (4.59 g, 26.09 mmol, 1.1 eq) and pyridine (35.58 mmol, 1.5 eq). The reaction mixture was stirred for 2 hours. Quenched with water and extracted with EtOAc. The organic phase was dried with anhydrous $Na_2SO_4$, filtered and the solvent was removed under reduced pressure. To this crude acyl adduct was added 2N NaOH (2.5 eq, 30 ml) then drop wise of di-n-propyl sulfate (4.3 g, 23.72 mmol, 1 eq). The mixture was heated at 50° C. for 1 hr. To this reaction mixture was added methanol (20 ml) and two more equivalents of 2N NaOH. The mixture was heated at reflux for 3 hours before cooled and acidified with HCl to pH ~7. The resulting precipitate was obtained by filtration and washed with water to give the desired product (5.89 g, 72%) after vacuum dried overnight at 40° C.: $^1$H NMR (400 MHz, DMSO-$d_6$) δ 14.1 (1H), 9.08 (1H), 8.48 (1H), 7.7 (1H), 4.00 (2H), 2.62 (1H), 1.78 (2H), 1.14 (2H), 0.92 (3H), 0.75 (2H); m/z (ES+) 346.79

The subject matter herein has been described with reference to various specific and preferred embodiments and techniques. However, it should be understood that that those skilled in the art may envision that variations and modifications may be made while remaining within the spirit and scope of the claims. It should also be understood that the various examples set forth herein have been included for purposes of illustration and should not be construed as limitations. Accordingly, the disclosure is not to be limited by what has been particularly shown and described, except as indicated by the appended claims.

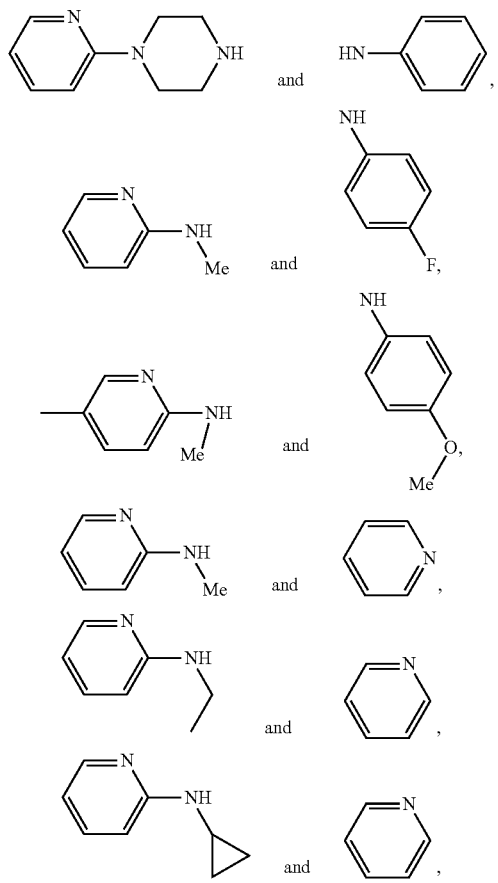

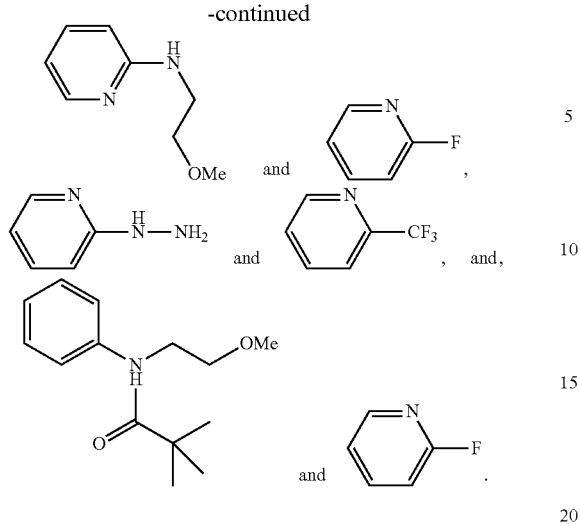

What is claimed is:

1. A process for preparing a compound of formula I:

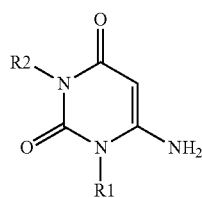

wherein:

R[1] and R[2] are independently ($C_1$-$C_8$)alkyl, ($C_3$-$C_8$)alkenyl, ($C_3$-$C_8$)alkynyl, ($C_1$-$C_8$)alkoxy, ($C_3$-$C_8$)cycloalkyl, ($C_3$-$C_8$)cycloalkyl($C_1$-$C_8$)alkyl-, ($C_4$-$C_{10}$) heterocycle, ($C_4$-$C_{10}$)heterocycle($C_1$-$C_8$)alkyl-, ($C_6$-$C_{10}$)aryl, ($C_6$-$C_{10}$)aryl($C_1$-$C_8$)alkyl-, ($C_5$-$C_{10}$) heteroaryl, or ($C_5$-$C_{10}$)heteroaryl($C_1$-$C_8$)alkyl-;

the process comprising:

a) reacting a monosubstituted urea of formula II

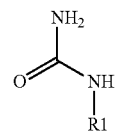

with ethyl-2-cyanoacetate in the presence of an alkoxide to produce an aminouracil of formula IIIa,

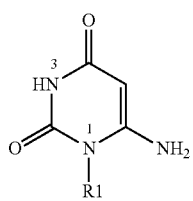

b) reacting the aminouracil of formula IIIa with dimethyl formamide-dimethyl acetal to produce a compound of formula IV,

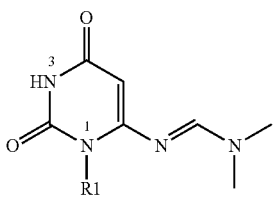

c) reacting the compound of formula IV with a $R^2$-boronic acid, a metal carbonate and a copper catalyst to produce a compound of formula V, and,

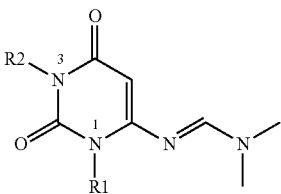

d) reacting the compound of formula V with an inert solvent and a metal hydroxide to produce the compound of formula I.

2. The process according to claim 1, wherein the alkoxide is a metal alkoxide selected from the group consisting of potassium tert-butoxide, sodium ethoxide, potassium ethoxide, calcium ethoxide, sodium tert-butoxide and combinations thereof.

3. The process according to claim 2, wherein the metal alkoxide is sodium ethoxide.

4. The process according to claim 1, wherein step b) is performed at a temperature of about 0° C. to about 100° C.

5. The process according to claim 4, wherein step b) is performed at a temperature of about 40° C.

6. The process according to claim 1, wherein step b) further includes an organic solvent selected from the group consisting of dimethylformamide, toluene, xylene and combinations thereof.

7. The process according to claim 1, wherein the copper catalyst is selected from the group consisting of copper bromide, copper iodide, copper acetate, copper chloride, copper carbonate, copper nitrate, copper sulfate, copper hydroxide, copper methylate and combinations thereof.

8. The process according to claim 7, wherein the copper catalyst comprises copper acetate.

9. The process according to claim 1, wherein the metal carbonate is selected from the group consisting of sodium carbonate, potassium carbonate, lithium carbonate, cesium carbonate, sodium bicarbonate, potassium bicarbonate, lithium bicarbonate, cesium bicarbonate and combinations thereof.

10. The process according to claim 9, wherein the compound of formula IV is reacted with the $R^2$-boronic acid, sodium carbonate and the copper catalyst.

11. The process according to claim 10, wherein step c) comprises reacting the compound of formula IV with a $R^2$-boronic acid, copper acetate and sodium carbonate in the presence of an amine ligand to produce the compound of formula V.

12. The process according to claim 1, wherein the inert solvent of step d) is methanol.

13. The process according to claim 1, wherein the metal hydroxide is selected from the group consisting of sodium hydroxide, potassium hydroxide, lithium hydroxide, magnesium hydroxide, calcium hydroxide and combinations thereof.

14. The process according to claim 13, wherein the metal hydroxide is sodium hydroxide.

15. The process according to claim 1 further comprising the step of:
e) reacting the compound of formula I with a nitration agent to produce a compound of formula VI,

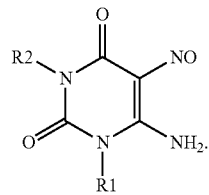

16. The process according to claim 15, wherein the nitration agent is selected from the group consisting of $NaNO_2/AcOH$, $HNO_3/H_2SO_4$, $N_2O_5/P_2O_5/CCl_4$, HONO, $EtONO_2$, $CH_3COONO_2$, $NO_2^+CF_3SO_3^-$ and combinations thereof.

17. The process according to claim 16, wherein the nitration agent is $NaNO_2/AcOH$.

18. The process according to claim 15 further comprising the step of:
f) reacting the compound of formula VI with an acylating agent of the formula R'—CO—W' to produce a compound of formula VII

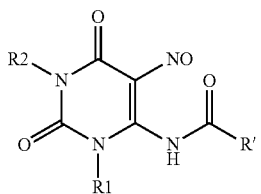

wherein R' is selected from the group consisting of hydrogen, halogen, substituted or unsubstituted ($C_1$-$C_8$) alkyl, ($C_3$-$C_8$)alkenyl, ($C_3$-$C_8$)alkynyl, ($C_1$-$C_8$)alkoxy, ($C_3$-$C_8$)cycloalkyl, ($C_3$-$C_8$)cycloalkyl($C_1$-$C_8$)alkyl-,($C_4$-$C_{10}$)heterocycle, ($C_4$-$C_{10}$) heterocycle ($C_1$-$C_8$)alkyl-, ($C_6$-$C_{10}$)aryl, ($C_6$-$C_{10}$)aryl($C_1$-$C_8$)alkyl-, ($C_5$-$C_{10}$)heteroaryl, ($C_5$-$C_{10}$)heteroaryl($C_1$-$C_8$)alkyl-, and -X($Z^1$)$_n$-Z;

X is a 5-10 member heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine (—N(R$^9$))- groups;

Z is —OR$^3$, —SR$^3$, halo, —S(O)$_m$—NR$^4$R$^5$, —NR$^4$R$^5$, or (C$_4$-C$_{10}$)heterocycle wherein the heterocycle is optionally substituted with 1, 2, 3, or 4 substituents independently selected from halo, cyano, nitro, —OR$^a$, —SR$^a$, (C$_1$-C$_8$)alkyl, (C$_6$-C$_{10}$)aryl, —O (C$_6$-C$_{10}$)aryl, hydroxy(C$_1$-C$_8$)alkyl, R$^b$R$^c$ N(C$_1$-C$_8$)alkyl, halo(C$_1$-C$_8$)alkyl, —NR$^b$R$^c$, —C(O)R$^a$, —COOR$^a$, or —C(O)NR$^b$R$^c$;

each Z$^1$ is independently (C$_1$-C$_8$)alkyl, (C$_2$-C$_8$)alkenyl, (C$_2$-C$_8$)alkynyl, -OR$^6$, —SR$^6$, halo, R$^6$O(C$_1$-C$_8$) alkyl, R$^7$R$^8$N(C$_1$-C$_8$)alkyl, halo(C$_1$-C$_8$)alkyl, —NR$^7$R$^8$, R$^7$R$^8$N(C$_1$-C$_8$)alkyl, —C(O)R$^6$, —COOR$^6$, or —C(O)NR$^7$R$^8$;

R$^3$ is (C$_1$-C$_8$)alkyl, (C$_3$-C$_8$)alkenyl, (C$_3$-C$_8$)alkynyl, (C$_6$-C$_{10}$)aryl, (C$_6$-C$_{10}$)aryl, (C$_1$-C$_8$)alkyl-, (C$_5$-C$_{10}$) heteroaryl, (C$_5$-C$_{10}$)heteroaryl(C$_1$-C$_8$)alkyl-, —C(O) R$^6$, or —C(O)NR$^7$R$^8$;

R$^4$ and R$^5$ are independently hydrogen, (C$_1$-C$_8$)alkyl, (C$_3$-C$_8$)alkenyl, (C$_3$-C$_8$)alkynyl, (C$_1$-C$_8$)alkoxy, (C$_3$-C$_8$)cycloalkyl, (C$_3$-C$_8$)cycloalkyl(C$_1$-C$_8$)alkyl-, (C$_6$-C$_{18}$) polycycloalkyl, (C$_6$-C$_{18}$)polycycloalkyl(C$_1$-C$_8$)alkyl-, (C$_3$-C$_{10}$)heterocycle, (C$_3$-C$_{10}$)heterocycle(C$_1$-C$_8$)alkyl -NR$^7$R$^8$, (C$_6$-C$_{10}$)aryl, (C$_6$-C$_{10}$)aryl (C$_1$-C$_8$)alkyl-, (C$_5$-C$_{10}$)heteroaryl, (C$_5$-C$_{10}$)heteroaryl(C$_1$-C$_8$)alkyl-, —(C$_2$-C$_4$—Y)$_q$—(CH$_2$)$_{2-4}$—X$^1$, —C(O)R$^6$, —CO$_2$R$^6$, —C(O)NR$^7$R$^8$, or —S(O)$_2$—NR$^7$R$^8$; or R$^4$ and R$^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy (—O—), thio (—S—), sulfinyl (—SO—), sulfonyl (—S(O)$_2$—) and amine —N(R$^9$)- in the ring, wherein the ring is optionally substituted with 1, 2, 3, or 4 substituents independently selected from halo, cyano, nitro, —OR$^a$, —SR$^a$, (C$_6$-C$_{10}$)aryl, —O (C$_6$-C$_{10}$)aryl, hydroxy(C$_1$-C$_8$)alkyl, R$^b$R$^c$N(C$_1$-C$_8$) alkyl, halo(C$_1$-C$_8$)alkyl, —NR$^b$R$^c$, —C(O)R$^a$, —COOR$^a$, and —C(O)NR$^b$R$^c$;

X$^1$ is —OR$^6$, —C(O)R$^6$, —CO$_2$R$^6$, or —NR$^7$R$^8$; and Y is oxy (—O—), thio (—S—), sulfinyl (—SO—), sulfonyl (—S(O)$_2$—) or amine —N(R$^9$)—;

wherein the alkyl, alkenyl, cycloalkyl, alkynyl, aryl, heterocycle, or heteroaryl groups of R$^1$, R$_2$, R$_3$, R$_4$ and R$^5$ groups are optionally substituted with one or more substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$ N(C$_1$-C$_8$)alkyl, halo (C$_1$-C$_8$)alkyl, —NR$^b$ R$^c$, —C(O)R$^a$, —COOR$^a$, or —C(O)NR$^b$R$^c$;

wherein R$^6$ is hydrogen, (C$_1$-C$_8$)alkyl, R$^a$O(C$_1$-C$_8$) alkyl, R$^b$ R$^c$ N(C$_1$-C$_8$)alkyl, halo(C$_1$-C$_8$)alkyl, (C$_3$-C$_{10}$)heterocycle, (C$_3$-C$_{10}$)heterocycle(C$_1$-C$_8$)alkyl-, (C$_6$-C$_{10}$)aryl, (C$_6$-C$_{10}$)aryl(C$_1$-C$_8$)alkyl-, (C$_4$-C$_{10}$) heteroaryl, or (C$_4$-C$_{10}$)heteroaryl(C$_1$-C$_8$)alkyl-; wherein the heterocycle, heteroaryl or aryl are optionally substituted with 1, 2, 3, or 4 substituents independently selected from halo, cyano, nitro, —OR$^a$, SR$^a$, (C$_6$-C$_{10}$)aryl —O(C$_6$-C$_{10}$)aryl, hydroxy(C$_1$-C$_8$) alkyl, R$^b$ R$^c$ N(C$_1$-C$_8$)alkyl, halo(C$_1$-C$_8$)alkyl, —NR$^b$R$^c$, —C(O)R$^a$, —COOR$^a$, or —C(O)NR$^b$ R$^c$;

wherein R$^7$, R$^8$ and R$^9$ are independently hydrogen, (C$_1$-C$_8$)alkyl, R$^a$ O(C$_1$-C$_8$)alkyl, R$^b$R$^c$N(C$_1$-C$_8$)alkyl, halo(C$_1$-C$_8$)alkyl, (C$_3$-C$_{10}$)heterocycle, (C$_6$-C$_{10}$) aryl, (C$_6$-C$_{10}$)aryl(C$_1$-C$_8$)alkyl-, (C$_4$-C$_{10}$)heteroaryl; —COOR$^a$, —C(O)R$^a$, or —C(O)NR$^b$R$^c$ wherein the heterocycle, heteroaryl or aryl are optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, or C(O)NR$^b$R$^c$; or R$^7$ and R$^8$ together with the atoms to which they are attached form a saturated or partially unsaturated, mono-, bicyclic- or aromatic ring having 3, 4, 5, 6, 7, or 8, ring atoms optionally having from 4 to eight ring atoms and optionally comprising 1, 2, 3, or 4 heteroatoms selected from non-peroxide oxy (—O—), thio (—S—), sulfinyl (—SO—), sulfonyl (—S(O)$_2$—) or amine —N(R$^b$)- in the ring;

R$^a$ is hydrogen, or (C$_1$-C$_6$)alkyl; R$^b$ and R$^c$ are each independently hydrogen, (C$_1$-C$_6$)alkyl, (C$_1$-C$_6$) alkoxy, (C$_3$-C$_8$)cycloalkyl, (C$_1$-C$_6$)alkylthio, (C$_6$-C$_{10}$)aryl, (C$_6$-C$_{10}$)aryl(C$_1$-C$_6$)alkyl-, heteroaryl, or heteroaryl(C$_1$-C$_6$)alkyl-; or R$^b$ and R$^c$ together with the nitrogen to which they are attached, form a pyrrolidyl, piperidyl, piperazinyl, azepinyl, diazepinyl, morpholinyl, or thiomorpholinyl ring;

W' is a leaving group;

where n is 0, 1, 2, 3, 4, 5, 6, 7, or 8; m is 1, or 2; and q is 1, 2, 3, or 4.

19. The process according to claim 18 wherein W' is a halogen.

20. The process according to claim 18 further comprising the step of:

g) reacting the compound of formula VII with a reducing agent in an aprotic solvent to produce a xanthine of formula VIII

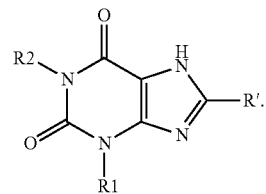

21. The process according to claim 20, wherein the reducing agent of step g) is hydrogen and palladium on carbon.

22. The process according to claim 21, wherein the reducing agent of step g) is sodium dithionite.

23. The process according to claim 22, wherein step g) further comprises an aprotic solvent selected from the group consisting of dimethyl sulfoxide, acetonitrile, acetone, dimethylformamide, ethyl acetate, tetrahydrofurn, dichloromethane and combinations thereof.

24. The process according to claim 23, wherein the aprotic solvent is dimethyl sulfoxide.

25. The process according to claim 15, further comprising the step of:

h) reacting the compound of formula VI with a reducing agent to produce the compound of formula XIV

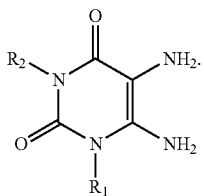

XIV

26. The process according to claim 25, wherein the reducing agent of step h) is hydrogen and palladium on carbon.

27. The process according to claim 25, wherein the reducing agent of step g) is sodium dithionite.

28. The process according to claim 25, further comprising the step of:
i) reacting the compound of formula XIV with a first acylating agent of the formula R'—CO—W' to produce the compound of formula XV

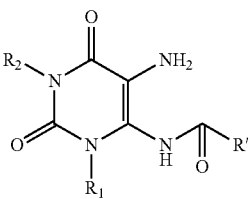

XV wherein R' is selected from the group consisting of hydrogen, halogen, substituted or unsubstituted $(C_1-C_8)$ alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4C_{10})$heterocycle$(C_1-C_8)$alkyl-, $(C_6-C_{10})$aryl, $(C_6-C_{10})$aryl$(C_1-C_8)$alkyl-, $(C_5-C_{10})$heteroaryl, $(C_510)$heteroaryl$(C_1-C_8)$alkyl-, and -X$(Z^1)_n$—Z;

X is a 5-10 member heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine (—N(R$^9$)—) groups;

Z is —OR$^3$, —SR$^3$, halo, —S(O)$_m$—NR$^4$R$^5$, —NR$^4$R$^5$, or $(C_4-C_{10})$heterocycle wherein the heterocycle is optionally substituted with 1, 2, 3, or 4 substituents independently selected from halo, cyano, nitro, —OR$^a$, —SR$^a$, $(C_1-C_8)$alkyl, $(C_6-C_{10})$aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, or —C(O)NR$^b$R$^c$;

each $Z^1$ is independently $(C_1-C_8)$alkyl, $(C_2-C_8)$alkenyl, $(C_2-C_8)$alkynyl, —OR$^6$, —SR$^6$, halo, R$^6$O(C$_1$-C$_8$) alkyl, R$^7$R$^8$N(C$_1$-C$_8$)alkyl, halo(C$_1$-C$_8$)alkyl, —NR$^7$R$^8$, R$^7$R$^8$N(C$_1$-C$_8$)alkyl, —C(O)R$^6$, —COOR$^6$, or —C(O)NR$^7$R$^8$;

R$^3$ is $(C_1-C_8)$alkyl, $(C_3-C_8)$alkenyl, $(C_3-C_8)$alkynyl, $(C_6-C_{10})$aryl, $(C_6-C_{10})$aryl(C-C$_8$)alkyl-, $(C_5-C_{10})$heteroaryl, $(C_5-C_{10})$heteroaryl$(C_1-C_8)$alkyl-, —C(O)R$^6$, or —C(O)NR$^7$R$^8$;

R$^4$ and R$^5$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_6-C_{18})$polycycloalkyl, $(C_6-C_{18})$polycycloalkyl$(C_1-C_8)$alkyl-, $(C_3-C_{10})$heterocycle, $(C_3-C_{10})$heterocycle $(C_1-C_8)$alkyl —NR$^7$R$^8$, $(C_6-C_{10})$aryl, $(C_6-C_{10})$aryl $(C_1-C_8)$alkyl-, $(C_5-C_{10})$heteroaryl, $(C_5-C_{10})$heteroaryl$(C_1-C_8)$alkyl-, —$(C_2-C_4$—Y$)_q$—(CH$_2$)$_{2-4}$—X$^1$, —C(O)R$^6$, —CO$_2$R$^6$, —C(O)NR$^7$R$^8$, or —S(O)$_2$—NR$^7$R$^8$; or R$^4$ and R$^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy (—O—), thio (—S—), sulfinyl (—SO—), sulfonyl (—S(O)$_2$—) and amine —N(R$^9$)—in the ring, wherein the ring is optionally substituted with 1, 2, 3, or 4 substituents independently selected from halo, cyano, nitro, —OR$^a$, —SR$^a$, $(C_6-C_{10})$aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

$X^1$ is —OR$^6$, —C(O)R$^6$, —CO$_2$R$^6$, or —NR$^7$R$^8$; and Y is oxy (—O—), thio (—S—), sulfinyl (—SO—), sulfonyl (—S(O)$_2$—) or amine —N(R$^9$)—;

wherein the alkyl, alkenyl, cycloalkyl, alkynyl, aryl, heterocycle, or heteroaryl groups of R$^1$, R$^2$, R$^2$, R$^3$, R$^4$and R$^5$ groups are optionally substituted with one or more substituents independently selected from halo, cyano, nitro, —OR$^a$, —SR$^a$, $(C_6-C_{10})$aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, or —C(O)NR$^b$R$^c$;

wherein R$^6$ is hydrogen, $(C_1-C_8)$alkyl, R$^a$O(C$_1$-C$_8$) alkyl, R$^b$R$^c$N(C$_1$-C$_8$)alkyl, halo(C$_1$-C$_8$)alkyl, $(C_3$-C$_{10})$heterocycle, $(C_3$-C$_{10})$heterocycle$(C_1$-C$_8$)alkyl-, $(C_6-C_{10})$aryl, $(C_6-C_{10})$aryl $(C_1-C_8)$alkyl-, $(C_4-C_{10})$ heteroaryl, or $(C_4-C_{10})$heteroaryl$(C_1-C_8)$alkyl-; wherein the heterocycle, heteroaryl or aryl are optionally substituted with 1, 2, 3, or 4 substituents independently selected from halo, cyano, nitro, —OR$^a$, SR$^a$, $(C_6-C_{10})$aryl —O(C$_6$-C$_{10}$)aryl, hydroxy(C$_1$-C$_8$) alkyl, R$^b$R$^c$N(C$_1$-C$_8$)alkyl, halo(C$_1$-C$_8$)alkyl, —NR$^b$R$^c$, —C(O)R$^a$, —COOR$^a$, or —C(O)NR$^b$R$^c$;

wherein R$^7$, R$^8$ and R$^9$ are independently hydrogen, $(C_1-C_8)$alkyl, R$^a$O(C$_1$-C$_8$)alkyl, R$^b$R$^c$N(C$_1$-C$_8$)alkyl, halo(C$_1$-C$_8$)alkyl, $(C_3$-C$_{10})$heterocycle, $(C_6-C_{10})$ aryl, $(C_6-C_{10})$aryl$(C_1-C_8)$alkyl-, $(C_4-C_{10})$heteroaryl; —COOR$^a$, —C(O)R$^a$, or —C(O)NR$^b$R$^c$ wherein the heterocycle, heteroaryl or aryl are optionally substituted with 1, 2, 3, or 4 substituents independently selected from halo, cyano, nitro, —OR$^a$, —SR$^a$, $(C_6$-C$_{10})$aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, or C(O)NR$^b$R$^c$; or R$^7$ and R$^8$ together with the atoms to which they are attached form a saturated or partially unsaturated, mono-, bicyclic- or aromatic ring having 3, 4, 5, 6, 7, or 8, ring atoms optionally having from 4 to eight ring atoms and optionally comprising 1, 2, 3, or 4 heteroatoms selected from non-peroxide oxy (—O—), thio (—S—), sulfinyl (—SO—), sulfonyl (—S(O)$_2$—) or amine —N(R$^b$)- in the ring;

R$^a$ is hydrogen, or $(C_1-C_6)$alkyl; R$^b$ and R$^c$ are each independently hydrogen, $(C_1-C_6)$alkyl, $(C_1-C_6)$ alkoxy, $(C_3-C_8)$cycloalkyl, $(C_1-C_6)$alkylthio, $(C_6-C_{10})$aryl, $(C_6-C_{10})$aryl$(C_1-C_6)$alkyl-, heteroaryl, or heteroaryl$(C_1-C_6)$alkyl-; or R$^b$ and R$^c$ together with the nitrogen to which they are attached, form a pyrrolidyl, piperidyl, piperazinyl, azepinyl, diazepinyl, morpholinyl, or thiomorpholinyl ring;

W' is a leaving group;
where n is 0, 1, 2, 3, 4, 5, 6, 7, or 8; m is 1, or 2; and q is 1, 2, 3, or 4.

29. The process according to claim 28, wherein R' is selected from the group consisting of:

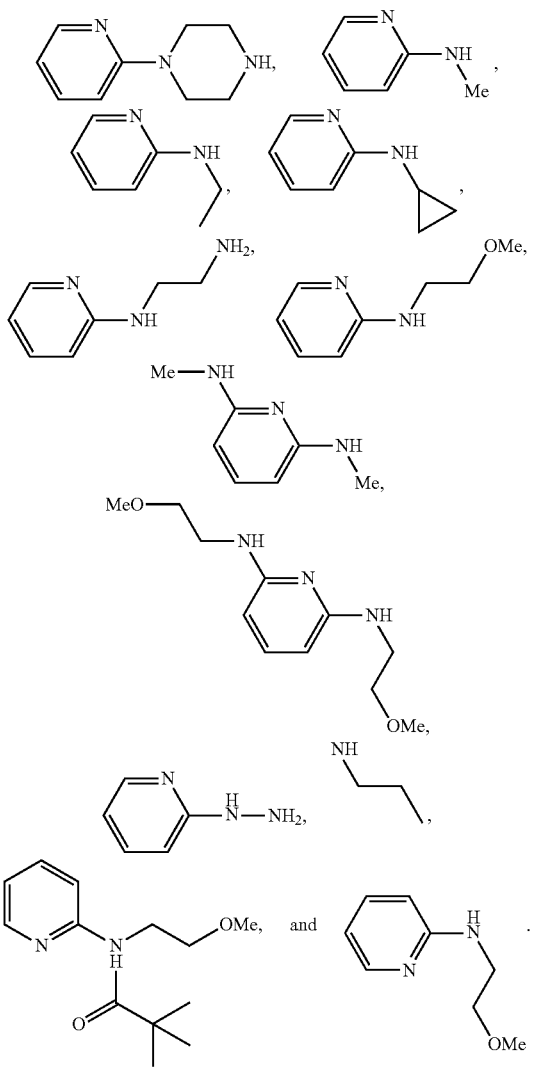

30. The process according to claim 28, further comprising the step of:
j) reacting the compound of formula XV with a metal hydroxide to produce the compound of formula VIII

VIII

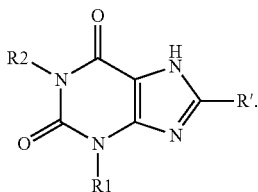

31. The process according to claim 30, wherein the metal hydroxide is selected from the group consisting of sodium hydroxide, potassium hydroxide, lithium hydroxide, magnesium hydroxide, calcium hydroxide and combinations thereof.

32. The process according to claim 30, wherein the metal hydroxide is sodium hydroxide.

33. The process according to claim 30, further comprising the step of:
k) reacting the compound of formula VIII with a second acylating agent of the formula R'''—CO—W''' to produce the compound of formula XVI

XVI

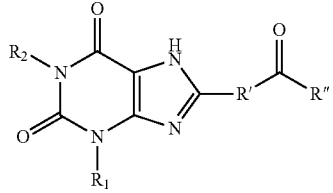

wherein R''' is selected from the group consisting of hydrogen, halogen, substituted or unsubstituted ($C_1$-$C_8$) alkyl, ($C_3$-$C_8$)alkenyl, ($C_3$-$C_8$)alkynyl, ($C_1$-$C_8$)alkoxy, ($C_3$-$C_8$)cycloalkyl, ($C_3$-$C_8$)cycloalkyl ($C_1$-$C_8$)alkyl-, ($C_4$-$C_{10}$)heterocycle, ($C_4$-$C_{10}$)heterocycle ($C_1$-$C_8$) alkyl-, ($C_6$-$C_{10}$)aryl, ($C_6$-$C_{10}$)aryl($C_6$-$C_8$)alkyl-, ($C_5$-$C_{10}$)heteroaryl, ($C_5$-$C_{10}$)heteroaryl ($C_1$-$C_8$)alkyl-, and -X($Z^1$)$_n$—Z;

X is a 5-10 member heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine (—N($R^9$)—) groups;

Z is —OR$^3$, —SR$^3$, halo, —S(O)$_m$, —NR$^4$R$^5$, —NR$^4$R$^5$, or ($C_4$-$C_{10}$)heterocycle wherein the heterocycle is optionally substituted with 1, 2, 3, or 4 substituents independently selected from halo, cyano, nitro, —OR$^a$, —SR$^a$, ($C_1$-$C_8$)alkyl, ($C_6$-$C_{10}$)aryl, —O($C_6$-$C_{10}$)aryl, hydroxy($C_1$-$C_8$)alkyl, R$^b$R$^c$N($C_1$-$C_8$)alkyl, halo($C_1$-$C_8$)alkyl, —NR$^b$R$^c$, —C(O)R$^a$, —COOR$^a$, or —C(O)NR$^b$R$^c$;

each $Z^1$ is independently ($C_1$-$C_8$)alkyl, ($C_2$-$C_8$)alkenyl, ($C_2$-$C_8$)alkynyl, —OR$^6$, —SR$^6$, halo, R$^6$O($C_1$-$C_8$) alkyl, R$^7$R$^8$N($C_1$-$C_8$)alkyl, halo($C_1$-$C_8$)alkyl, —NR$^7$R$^8$, R$^7$R$^8$N($C_1$-$C_8$)alkyl, —C(O)R$^6$, —COOR$^6$, or —C(O)NR$^7$R$^8$;

R$^3$ is ($C_1$-$C_8$)alkyl, ($C_3$-$C_8$)alkenyl, ($C_3$-$C_8$)alkynyl, ($C_6$-$C_{10}$)aryl, ($C_6$-$C_{10}$)aryl($C_1$-$C_8$)alkyl-, ($C_5$-$C_{10}$) heteroaryl, ($C_5$-$C_{10}$)heteroaryl($C_1$-$C_8$)alkyl-, —C(O)R$^6$, or —C(O)NR$^7$R$^8$;

R$^4$ and R$^5$ are independently hydrogen, ($C_1$-$C_8$)alkyl, ($C_3$-$C_8$)alkenyl, ($C_3$-$C_8$)alkynyl, ($C_1$-$C_8$)alkoxy, ($C_3$-$C_8$)cycloalkyl, ($C_3$-$C_8$)cycloalkyl($C_1$-$C_8$)alkyl-, ($C_6$-$C_{18}$)polycycloalkyl, ($C_6$-$C_{18}$)polycycloalkyl ($C_1$-$C_8$)alkyl-, ($C_3$-$C_{10}$)heterocycle, ($C_3$-$C_{10}$)heterocycle($C_1$-$C_8$)alkyl —NR$^7$R$^8$, ($C_6$-$C_{10}$)aryl, ($C_6$-$C_{10}$)aryl($C_1$-$C_8$)alkyl-, ($C_5$-$C_{10}$)heteroaryl, ($C_5$-$C_{10}$)heteroaryl($C_1$-$C_8$)alkyl-, —($C_2$-$C_4$—Y)$_q$ —(CH$_2$)$_{2-4}$—X$^1$, —C(O)R$^6$, —CO$_2$R$^6$, —C(O)NR$^7$R$^8$, or —S(O)$_2$—NR$^7$R$^8$; or R$^4$ and R$^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy (—O—), thio (—S—), sulfinyl (—SO—), sulfonyl (—S(O)₂—) and amine —N(R⁹)— in the ring, wherein the ring is optionally substituted with 1, 2, 3, or 4 substituents independently selected from halo, cyano, nitro, —ORᵃ, —SRᵃ, (C₆-C₁₀)aryl, —O(C₆-C₁₀)aryl, hydroxy(C₁-C₈)alkyl, RᵇRᶜN(C₁-C₈)alkyl, halo(C₁-C₈)alkyl, —NRᵇRᶜ, —C(O)Rᵃ, —COORᵃ, and —C(O)NRᵇRᶜ;

X¹ is —OR⁶, —C(O)R⁶, —CO₂R⁶, or —NR⁷R⁸; and Y is oxy (—O—), thio (—S—), sulfinyl (—SO—), sulfonyl (—S(O)₂—) or amine —N(R⁹)—;

wherein the alkyl, alkenyl, cycloalkyl, alkynyl, aryl, heterocycle, or heteroaryl groups of R¹, R², R³, R⁴ and R⁵ groups are optionally substituted with one or more substituents independently selected from halo, cyano, nitro, —ORᵃ, —SRᵃ, (C₆-C₁₀)aryl, —O(C₆-C₁₀)aryl, hydroxy(C₁-C₈)alkyl, RᵇRᶜN(C₁-C₈)alkyl, halo(C₁-C₈)alkyl, —NRᵇRᶜ, —C(O)Rᵃ, —COORᵃ, or —C(O)NRᵇRᶜ;

wherein R⁶ is hydrogen, (C₁-C₈)alkyl, RᵃO(C₁-C₈)alkyl, RᵇRᶜN(C₁-C₈)alkyl, halo(C₁-C₈)alkyl, (C₃-C₁₀)heterocycle, (C₃-C₁₀)heterocycle(C₁-C₈)alkyl-, (C₆-C₁₀)aryl, (C₆-C₁₀)aryl(C₁-C₈)alkyl-, (C₄-C₁₀)heteroaryl, or (C₄-C₁₀)heteroaryl(C₁-C₈)alkyl-; wherein the heterocycle, heteroaryl or aryl are optionally substituted with 1, 2, 3, or 4 substituents independently selected from halo, cyano, nitro, —ORᵃ, SRᵃ, (C₆-C₁₀)aryl —O(C₆-C₁₀)aryl, hydroxy(C₁-C₈)alkyl, RᵇRᶜN(C₁-C₈)alkyl, halo(C₁-C₈)alkyl, —NRᵇRᶜ, —C(O)Rᵃ, —COORᵃ, or —C(O)NRᵇRᶜ;

wherein R⁷, R⁸ and R⁹ are independently hydrogen, (C₁-C₈)alkyl, Rᵃ O(C₁-C₈)alkyl, RᵇRᶜN(C₁-C₈)alkyl, halo(C₁-C₈)alkyl, (C₃-C₁₀)heterocycle, (C₆-C₁₀)aryl (C₆-C₁₀)aryl(C₁-C₈)alkyl-, (C₄-C₁₀)heteroaryl; —COORᵃ, —C(O)Rᵃ, or —C(O)NRᵇRᶜ wherein the heterocycle, heteroaryl or aryl are optionally substituted with 1, 2, 3, or 4 substituents independently selected from halo, cyano, nitro, —ORᵃ, —SRᵃ, (C₆-C₁₀)aryl, —O(C₆-C₁₀)aryl, hydroxy(C₁-C₈)alkyl, RᵇRᶜN(C₁-C₈)alkyl, halo(C₁-C₈)alkyl, —NRᵇRᶜ, —C(O)Rᵃ, —COORᵃ, or C(O)NRᵇRᶜ; or R⁷ and R⁸ together with the atoms to which they are attached form a saturated or partially unsaturated, mono-, bicyclic- or aromatic ring having 3, 4, 5, 6, 7, or 8, ring atoms optionally having from 4 to eight ring atoms and optionally comprising 1, 2, 3, or 4 heteroatoms selected from non-peroxide oxy (—), thio (—S—), sulfinyl (—SO—), sulfonyl (—S(O)₂—) or amine —N(Rᵇ)— in the ring;

Rᵃ is hydrogen, or (C₁-C₆)alkyl; Rᵇ and Rᶜ are each independently hydrogen, (C₁-C₆)alkyl, (C₁-C₆) alkoxy, (C₃-C₈)cycloalkyl, (C₁-C₆)alkylthio, (C₆-C₁₀)aryl, (C₆-C₁₀)aryl(C₁-C₆)alkyl-, heteroaryl, or heteroaryl(C₁-C₆)alkyl-; or Rᵇ and Rᶜ together with the nitrogen to which they are attached, form a pyrrolidyl, piperidyl, piperazinyl, azepinyl, diazepinyl, morpholinyl, or thiomorpholinyl ring;

W" is a leaving group;

where n is 0, 1, 2, 3, 4, 5, 6, 7, or 8; m is 1, or 2; and q is 1, 2, 3, or 4.

34. The process according to claim 33, wherein R" is selected from the group consisting of

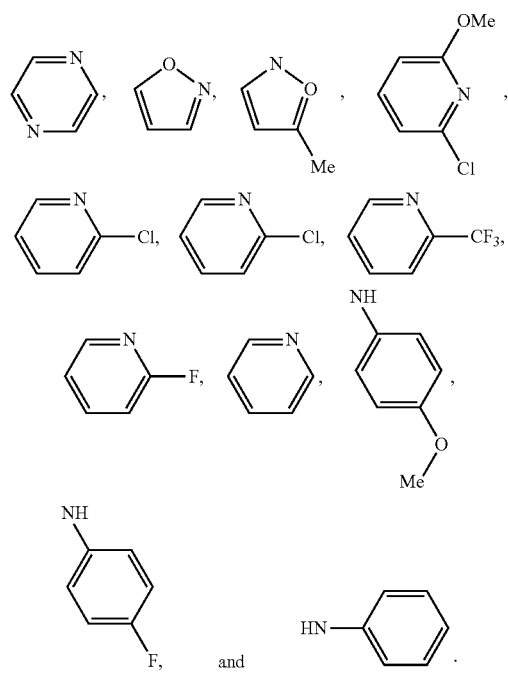

35. The process according to claim 33, wherein R' and R" are selected from the following pairs: